US010126295B2

(12) United States Patent
Saavedra

(10) Patent No.: US 10,126,295 B2
(45) Date of Patent: Nov. 13, 2018

(54) METHOD FOR TREATING PULMONARY EXACERBATION AND DISEASE PROGRESSION IN SUBJECTS HAVING CYSTIC FIBROSIS

(71) Applicant: National Jewish Health, Denver, CO (US)

(72) Inventor: Milene Saavedra, Denver, CO (US)

(73) Assignee: National Jewish Health, Denver, CO (US)

( * ) Notice: Subject to any disclaimer, the term of this patent is extended or adjusted under 35 U.S.C. 154(b) by 491 days.

(21) Appl. No.: 14/665,331

(22) Filed: Mar. 23, 2015

(65) Prior Publication Data

US 2015/0322520 A1    Nov. 12, 2015

Related U.S. Application Data

(60) Provisional application No. 62/000,903, filed on May 20, 2014, provisional application No. 61/968,960, filed on Mar. 21, 2014.

(51) Int. Cl.
| | | |
|---|---|---|
| *C12P 19/34* | (2006.01) | |
| *G01N 33/537* | (2006.01) | |
| *C12Q 1/6883* | (2018.01) | |
| *G01N 33/68* | (2006.01) | |
| *G06F 19/24* | (2011.01) | |
| *G16H 50/30* | (2018.01) | |
| *G06F 19/00* | (2018.01) | |

(52) U.S. Cl.
CPC ......... *G01N 33/537* (2013.01); *C12Q 1/6883* (2013.01); *G01N 33/68* (2013.01); *G01N 33/6893* (2013.01); *G06F 19/00* (2013.01); *G06F 19/24* (2013.01); *G06F 19/70* (2013.01); *G16H 50/30* (2018.01); *C12Q 2600/118* (2013.01); *C12Q 2600/158* (2013.01); *C12Q 2600/16* (2013.01); *G01N 2333/54* (2013.01); *G01N 2333/705* (2013.01); *G01N 2333/70503* (2013.01); *G01N 2333/70535* (2013.01); *G01N 2333/70596* (2013.01); *G01N 2333/924* (2013.01); *G01N 2333/96486* (2013.01); *G01N 2400/40* (2013.01); *G01N 2800/122* (2013.01); *G01N 2800/125* (2013.01); *G01N 2800/127* (2013.01); *G01N 2800/50* (2013.01)

(58) Field of Classification Search
USPC ............................................. 435/6.12, 91.2
See application file for complete search history.

(56) References Cited

U.S. PATENT DOCUMENTS

| | | | |
|---|---|---|---|
| 8,101,361 B2 | 1/2012 | Saavedra et al. | |
| 8,465,923 B2 | 6/2013 | Saavedra et al. | |
| 9,624,543 B2* | 4/2017 | Saavedra | ............ C12Q 1/6883 |
| 2005/0113345 A1 | 5/2005 | Chow et al. | |
| 2005/0214871 A1 | 9/2005 | Boon et al. | |
| 2008/0226645 A1 | 9/2008 | O'Toole | |
| 2014/0005099 A1 | 1/2014 | Saavedra et al. | |
| 2016/0068909 A1 | 3/2016 | Saavedra | |
| 2017/0102395 A1* | 4/2017 | Saavedra | ............ C12Q 1/6883 |

FOREIGN PATENT DOCUMENTS

| | | |
|---|---|---|
| WO | WO 2004/010139 | 1/2004 |
| WO | WO 2008/023446 | 2/2008 |

OTHER PUBLICATIONS

"measure," The Free Dictionary, 2014, retrieved from www.thefreedictionary.com/measuring, retrieved on Mar. 18, 2014, 3 pages.
Burns et al., "Effect of Chronic Intermittent Administration of Inhaled Toberamycin on Respiratory Microbial Flora in Patents with Cystic Fibrosis," Journal of Infectious Diseases, 1999, vol. 179, pp. 1190-1196.
Coleman "Of mouse and man—what is the value of the mouse in predicting gene expression in humans?" Drug Discovery Today, Mar. 2003, vol. 8, No. 6, pp. 233-235.
Cunningham et al., "Duration of Effect of Intravenous Antibiotics on Spriometry and Sputum Cytokines in Children with Cystic Fibrosis", Pediatric Pulmonology 36:43-48 (2003).
Gray et al. "Sputum and serum calprotectin are useful biomarkers during CF exacerbation," Journal of Cystic Fibrosis, May 2010, vol. 9, No. 3, pp. 193-198.
Gupta "Comparative Gene Expression Profiling of Mediators of Inflammation in COPD versus Asthma Patients: Screening for Potential Pharmacodynamic Response Markers." AAPS PharmSci 3 Meeting Abstracts, 2001, vol. 4, Supplemental #M2311.
Hansel "Oligonucleotide-microarray analysis of peripheral-blood lymphocytes in severe asthma." The Journal of Laboratory and Clinical Medicine, May 2005, pp. 263-274.

(Continued)

*Primary Examiner* — Kenneth R Horlick
(74) *Attorney, Agent, or Firm* — Sheridan Ross P.C.

(57) ABSTRACT

The present invention is related to a method for determining pulmonary disease progression severity in a subject having cystic fibrosis and treating the subject according to the severity. The method comprises obtaining a whole blood sample from the subject; detecting the mRNA expression level of each of the following genes: TLR2, ADAM9, PLXND1, CD163, CD36, CD64, CSPG2, IL32, HPSE, HCA112; determining the severity of the pulmonary disease progression based on the subject's combined mRNA expression level of the genes; and treating the subject.

7 Claims, 16 Drawing Sheets

(56) References Cited

OTHER PUBLICATIONS

Hubeau et al., "Quantitative analysis of inflammatory cells infiltrating the cystic fibrosis airway mucosa", Clin Exp Immunol 2001; 124:69-76.

Kowal et al., "Differential expression of monocyte CD163 in single- and dual-asthmatic responders during allergen-induced bronchoconstriction," Clinical and Experimental Allergy, 2006, vol. 36, No. 12, 1584-1591.

Liou et al. "Sputum Biomarkers and the Prediction of Clinical Outcomes in Patients with Cystic Fibrosis," PLOS ONE, Aug. 2012, vol. 7, No. 8, e42748, 11 pages.

Liu et al. "Comparison of differentially expressed genes in T lymphocytes between human autoimmune disease and murine models of autoimmune disease." Clinical Immunology, Sep. 2004, vol. 112, No. 3, pp. 225-230.

Min et al. "Variability of gene expression profiles in human blood and lymphoblastoid cell lines." BMC Genomics, Feb. 2010, vol. 11, 14 pages.

Moffitt et al. "Inflammatory and immunological biomarkers are not related to survival in adults with Cystic Fibrosis," Journal of Cystic Fibrosis, Jan. 2014, vol. 13, No. 1, pp. 63-68.

Moller et al. "Macrophage serum markers in pneumococcal bacteremia: Prediction of survival by soluble CD163." Critical Care Med, Oct. 2006, vol. 34, No. 10, pp. 2561-6, (Abstract Only).

Nick et al. "Blood mRNA biomarkers for detection of treatment response in acute pulmonary exacerbations of cystic fibrosis," Thorax, Oct. 2013, vol. 68, No. 10, pp. 929-937.

Nixon et al., "Circulating Immunoreactive Interleukin-6 in Cystic Fibrosis", Am J Respir Crit Care Med, vol. 157, pp. 1764-1769, 1998.

Ordoñez et al., "Inflammatory and Microbiologic Markers in Induced Sputum after Intravenous Antibiotics in Cystic Fibrosis", American Journal of Respiratory and Critical Care Medicine, vol. 168, 2003, pp. 1471-1475.

28 Palmer "Cell-type specific gene expression profiles of leukocytes in human peripheral blood" BMC Genomics, May 2006, vol. 7, 15 pages.

Pons et al., "Expression of Toll-like receptor 2 is up-regulated in monocytes from patients with chronic obstructive pulmonary disease," Respiratory Research. 2006, vol. 7, No. 64, pp. 1-9.

Ramilo et al., "Gene expression patterns in blood leukocytes discriminate patients with acute infections", 2007, 109:2066-2077.

Redecke et al., "Cutting Edge: activation of Toll-like receptor 2 induces a Th2 immune response and promotes experimental asthma," The Journal of Immunology, 2004, vol. 172, No. 5, pp. 2739-2743.

Reix et al., "Cytokine pattern in cystic fibrosis patients during antibiotic therapy and gene therapy using adenoviral vector", European Cytokine Network, vol. 13, No. 3, 324-30, Sep. 2002, articles originaux.

Saavedra et al. "Circulating RNA Transcripts Identify Therapeutic Response in Cystic Fibrosis Lung Disease," American Jounal of Respiratory and Critical Care Medicine, Nov. 2008, vol. 178, No. 9, pp. 929-938.

Saetre et al. "From wild wolf to domestic dog: gene expression changes in the brain." Molecular Brain Research, Jul. 2004, vol. 126, No. 2, pp. 198-206.

Saiman et al., "Azithromycin in Patients With Cystic Fibrosis Chromically Infected With Pseudomonas aeruginosa," JAMA, 2003, vol. 290(13), pp. 1749-1756.

Shoki et al. "Systematic Review of Blood Biomarkers in Cystic Fibrosis Pulmonary Exacerbations," Chest, Nov. 2013, vol. 144, No. 5, pp. 1659-1670.

Weiss et al., "Soluble CD163: An age-dependent, anti-inflammatory biomarker predicting outcome in sepsis", Crit Care Med 2006 vol. 34, No. 10, pp. 2682-2683.

Wojewodka et al. "Candidate Markers Associated with the Probability of Future Pulmonary Exacerbations in Cystic Fibrosis Patients," PLOS ONE, Feb. 2014, vol. 9, No. 2, e88567, 12 pages.

Wolter et al., "Cytokines and Inflammatory Mediators Do Not Indicate Acute Infection in Cystic Fibrosis", Clinical and Diagnostic Laboratory Immunology, Mar. 1999, p. 260-265.

Woodruff "Genome-wide profiling identifies epithelial cell genes associated with asthma and with treatment response to corticosteroids." PNAS, Oct. 2, 2007, vol. 104, No. 40, pp. 15858- 15863.

Wright et al., "Respiratory Epithelial Gene Expression in Patients with Mild and Severe Cystic Fibrosis Lung Disease," American Journal of Respiratory Cell and Molecular Biology, 2006, vol. 35, Iss. 3, pp. 327-336.

Wu et al., "Toll-like Receptor 2 Down-regulation in Established Mouse Allergic Lungs Contributes to Decreased Mycoplasma Clearance", Am J Respir Crit Care Med vol. 1777, pp. 720-729, 2008.

* cited by examiner

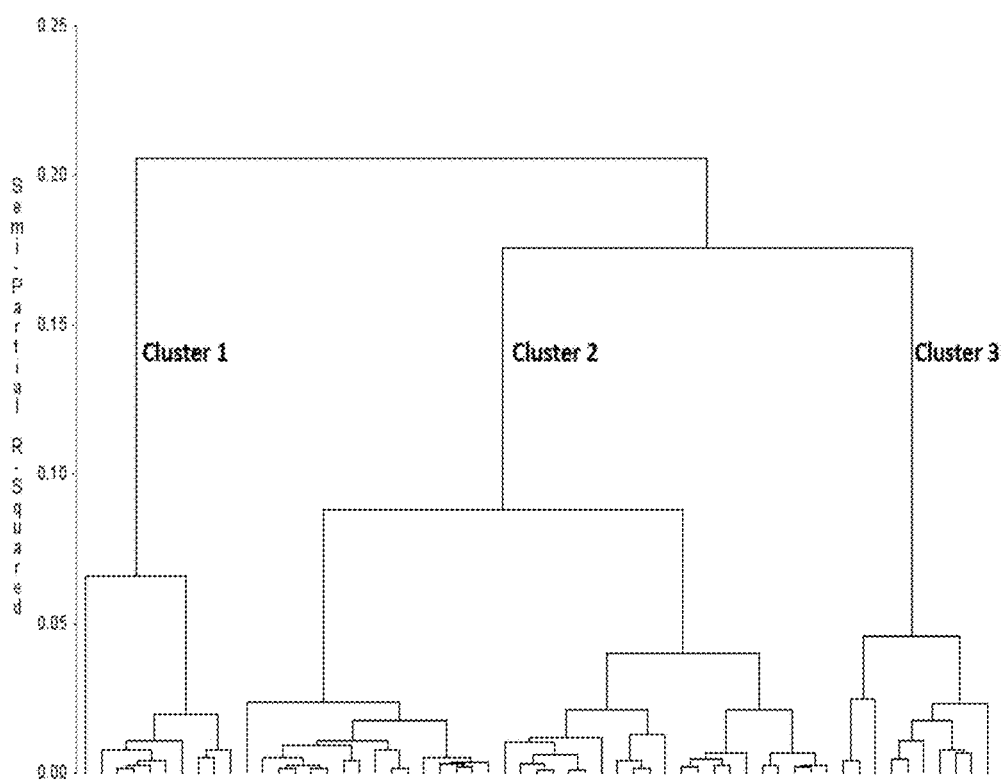

METHOD FOR TREATING PULMONARY EXACERBATION AND DISEASE PROGRESSION IN SUBJECTS HAVING CYSTIC FIBROSIS

CROSS REFERENCE TO RELATED APPLICATIONS

This application claims the benefit of priority under 35 U.S.C. § 119(e) to U.S. Provisional Patent Application Ser. No. 61/968,960, filed Mar. 21, 2014 and to U.S. Provisional Patent Application Ser. No. 62/000,903, filed May 20, 2014, which are incorporated herein by reference.

FIELD OF THE INVENTION

The field of the present invention involves the categorization and treatment of a population of subjects that are at risk for increased pulmonary exacerbation and disease progression including an increase in morbidity and/or mortality associated with severe pulmonary exacerbation.

BACKGROUND

Cystic fibrosis (CF) impacts 30,000 individuals in the United States and 70,000 individuals worldwide (Patient registry: Annual Data Report. Cystic Fibrosis Foundation 2012; Bethesda, Md.). Mortality from the disease primarily occurs due to progressive respiratory infection and an excessive inflammatory response in the CF lung (Davis P B, Drumm M, Konstan M W. Cystic fibrosis. Am J Respir Crit Care Med 1996; 154:1229-56; Chmiel J F, Berger M, Konstan M W. The role of inflammation in the pathophysiology of CF lung disease. Clin Rev Allergy Immunol 2002; 23:5-27). As the disease progresses, patients experience increasingly frequent pulmonary exacerbations, which in turn increase risk for subsequent decline (Sanders D B, Hoffman L R, Emerson J, et al. Return of FEV1 after pulmonary exacerbation in children with cystic fibrosis. Pediatr Pulmonol 2010; 45:127-34; Sanders D B, Bittner R C, Rosenfeld M, Hoffman L R, Redding G J, Goss C H. Failure to recover to baseline pulmonary function after cystic fibrosis pulmonary exacerbation. Am J Respir Crit Care Med 2010; 182:627-3; Waters V, Stanojevic S, Atenafu E G, et al. Effect of pulmonary exacerbations on long-term lung function decline in cystic fibrosis. Eur Respir J 2012; 40:61-6). The number of pulmonary exacerbation episodes suffered in a single year correlates highly with lung function decline in the ensuing three years for both children and adults (Sanders D B, Hoffman L R, Emerson J, et al. Return of FEV1 after pulmonary exacerbation in children with cystic fibrosis. Pediatr Pulmonol 2010; 45:127-34; Sanders D B, Bittner R C, Rosenfeld M, Hoffman L R, Redding G J, Goss C H. Failure to recover to baseline pulmonary function after cystic fibrosis pulmonary exacerbation. Am J Respir Crit Care Med 2010; 182:627-32; Sanders D B, Bittner R C, Rosenfeld M, Redding G J, Goss C H. Pulmonary exacerbations are associated with subsequent FEV1 decline in both adults and children with cystic fibrosis. Pediatr Pulmonol 2011; 46:393-400). An exceedingly high number of CF patients, 1 in 4, do not recover to baseline Forced Expiratory Volume in 1 second ($FEV_1$) after standard treatment of acute pulmonary exacerbations (APE) (Sanders D B, Hoffman L R, Emerson J, et al. Return of FEV1 after pulmonary exacerbation in children with cystic fibrosis. Pediatr Pulmonol 2010; 45:127-34).

Cystic fibrosis (CF) is the most common lethal inherited disease in the western world. While life expectancies have increased to nearly 40 years, respiratory failure still accounts for >80% of deaths from the disease, usually in young adults in the third or fourth decade of life. The triad of airway obstruction with mucus, chronic endobronchial infection with pathogens such as Pseudomonas aeruginosa, and severe airway inflammation, are the major pathogenic factors in CF lung disease (Konstan, 1998, Clin Chest Med 19(3):505-13, vi). Given the shortage of solid organs for transplantation in end stage lung disease, there is a critical need for effective anti-microbial and anti-inflammatory therapies to mitigate progression of disease in this young population.

The rendering of rapid and efficient clinical trials in CF and other diseases associated with pulmonary exacerbation, is hampered, in part, by the lack of sensitive measures of treatment response. In general, severity of exacerbation episodes are estimated based on spirometry and symptoms (Shoki A H, Mayer-Hamblett N, Wilcox P G, Sin D D, Quon B S. Systematic review of blood biomarkers in cystic fibrosis pulmonary exacerbations. Chest 2013; 144:1659-70). No mechanism exists to quantify or to "stage" the degree of inflammation in a particular individual, in a manner which predicts their risk from the infectious episode. Such a tool could potentially capture the marked heterogeneity in exacerbations between individuals, as well as within an individual, from one episode to another. Identification of molecular phenotypes underlying exacerbation heterogeneity would improve understanding of the individual host's response to pulmonary infection, ideally allowing customization of treatment approaches during the episode and beyond it. In current practice, consensus guidelines for APE treatment are relatively limited, in part due to a lack of definitions and classifiers of APE severity. There are no class A recommendations, and recommendations regarding key aspects of treatment are deemed "indeterminate" for the following: drug selection, quantity of antimicrobial agents, dosing strategies, and duration of antibiotics (Flume P A, Mogayzel P J, Jr., Robinson K A, et al. Cystic fibrosis pulmonary guidelines: treatment of pulmonary exacerbations. Am J Respir Crit Care Med 2009; 180:802-8). The ability to readily identify and quantify host inflammatory responses may allow stratification of treatment according to underlying biology, facilitating the conduct of clinical trials to identify strategies to improve current APE outcomes.

At present, there are no known reliable and sensitive molecular markers which can be used to categorize subject subgroups at risk for increased pulmonary exacerbation and/or disease progression, including increased risk of mortality and/or morbidity due to severe acute pulmonary exacerbation. There is a critical need in CF to better understand the impact a particular exacerbation has on a patient's overall disease course.

SUMMARY OF INVENTION

One embodiment of the invention relates to a method for categorizing a subject at risk for increased pulmonary exacerbation disease progression wherein the subject has experienced a pulmonary exacerbation, the method comprising (a) obtaining a biological sample from the subject; (b) detecting the expression level of one or more genes selected from the group consisting of TLR2, ADAM2, PLXND1, CD163, CD36, CD64, CSPG2, IL32, HPSE, HCA112 and combinations thereof; (c) comparing the expression level of the one or more genes from the subject with gene expression profiles of the same genes known to correlate with increased pulmonary exacerbation disease progression; and (d) categorizing the subject as at increased risk for increased pulmonary exacerbation disease progression when the subject's gene expression profile correlates to the gene expression profile for increased pulmonary exacerbation disease progression.

In one aspect of this embodiment, a subject identified as having an increased risk for pulmonary exacerbation disease progression will have an increased risk of morbidity.

In one aspect of this embodiment, a subject identified as having an increased risk for pulmonary exacerbation disease progression will have an increased risk of mortality.

In one aspect of this embodiment, a subject identified as having an increased risk for pulmonary exacerbation disease progression will have an increased risk for exacerbation recurrence.

In one aspect of this embodiment, a subject identified as having an increased risk for pulmonary exacerbation disease progression will have a shorter interval of exacerbation free time.

In one aspect of this embodiment, the method further comprises measuring the subject's forced expiratory volume ($FEV_1$) and/or C-reactive protein (CRP) levels.

Another embodiment of the invention relates to a method to treat a subject at risk for increased pulmonary exacerbation wherein the subject has experienced a pulmonary exacerbation, the method comprising: (a) obtaining a biological sample from the subject; (b) detecting the expression level of one or more genes selected from the group consisting of TLR2, ADAM9, PLXND1, CD163, CD36, CD64, CSPG2, IL32, HPSE, HCA112 and combinations thereof; (c) comparing the expression level of the one or more genes from the subject with gene expression profiles of the same genes known to correlate with increased pulmonary exacerbation, wherein certain expression profiles identify the subject as at increased risk for increased pulmonary exacerbation; and (d) treating the subject aggressively if the subject is at risk for increased pulmonary exacerbation.

In one aspect of this embodiment, the subject identified as having an increased risk for pulmonary exacerbation will have an increased risk of morbidity, mortality, and/or an increased risk for exacerbation recurrence.

In one aspect of any of the embodiments, the subject has been diagnosed as having a disease selected from the group consisting of cystic fibrosis, asthma, chronic pulmonary obstructive disease, emphysema, interstitial lung disease, bronchitis, acute respiratory distress syndrome, and pneumonia. In one aspect, the subject has been diagnosed as having cystic fibrosis.

In one aspect of any of the embodiments, the biological sample is whole blood, Peripheral Blood Mononuclear Cells (PBMCs), leukocytes, monocytes, lymphocytes, basophils, or eosinophils. In one aspect, the biological sample is whole blood.

In one aspect of any of the embodiments, the expression level of the one or more genes is detected by quantitative PCR or flow cytometery.

In yet another aspect of the embodiments, the expression level of each of the following genes TLR2, ADAM9, PLXND1, CD163, CD36, CD64, CSPG2, IL32, HPSE, and HCA112 is detected and compared.

BRIEF DESCRIPTION OF THE DRAWINGS

FIG. 1 shows hierarchical cluster analysis of CF peripheral blood samples at the onset of acute pulmonary exacerbation (AEP). Cluster analysis from leukocytes categorizes three distinct molecular clusters of gene expression, based on a 10-gene panel (cluster of differentiation 64 (CD64), a disintegrin and metalloproteinase domain 9 (ADAMS), cluster of differentiation 36 (CD36), interleukin 32 (IL32), heparanase (HPSE), plexin D1 (PLXND1), hepatocellular carcinoma associated antigen 112 (HCA112), versican (CSPG2), toll-like receptor 2 (TLR2), and cluster of differentiation 163 (CD163)), with corresponding sample sizes of n=10 (cluster 1), n=37 (cluster 2), and n=10 (cluster 3).

DETAILED DESCRIPTION

Figure 2A:
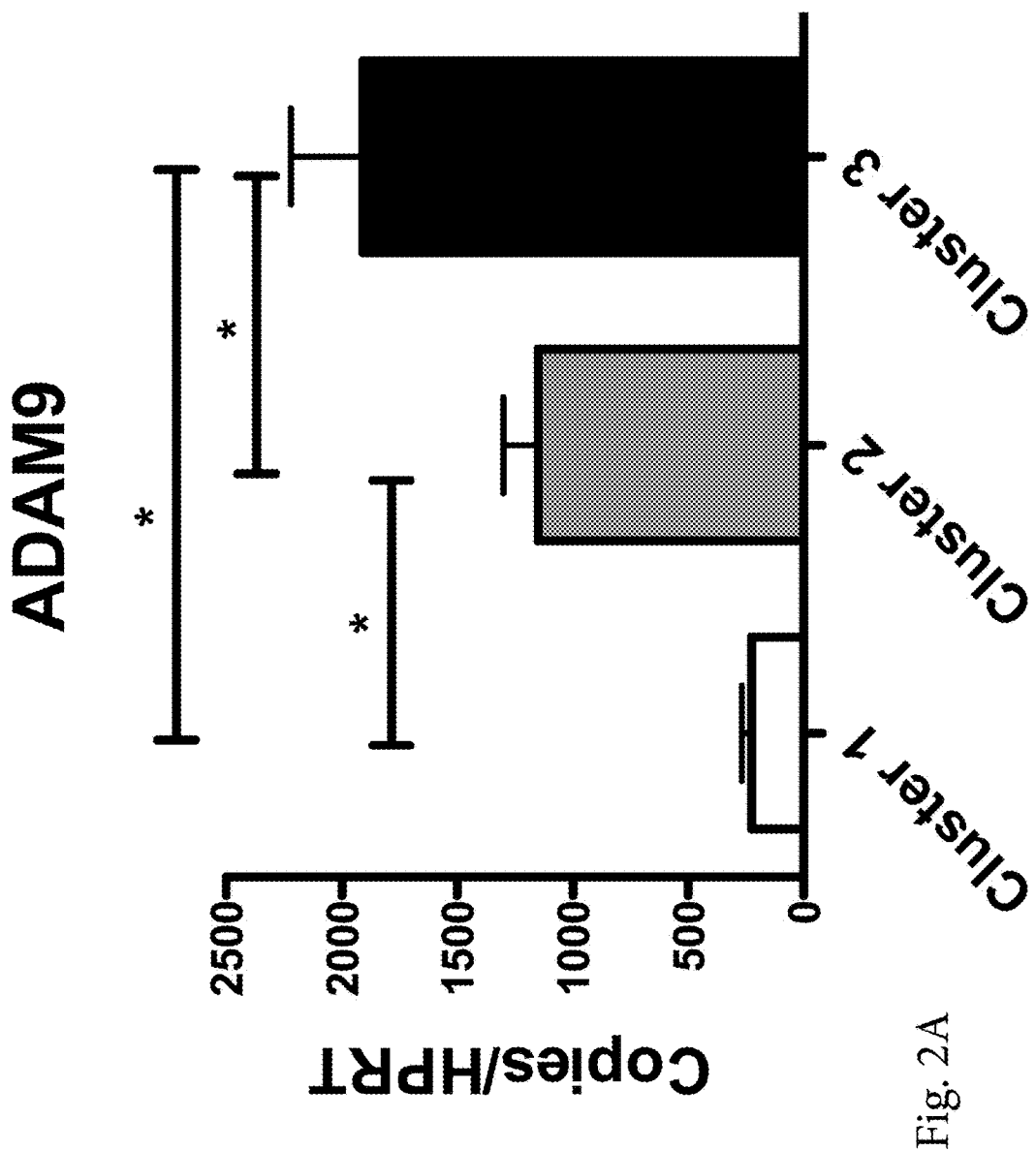
FIGS. 2A to 2J show the comparison of mean expression values of a 10-gene panel between clusters. Error bars represent SEM. *p<0.05 based on ANOVA analysis of log-transformed values with Tukey's Multiple Comparison Test for differences between clusters.
Figure 2B:
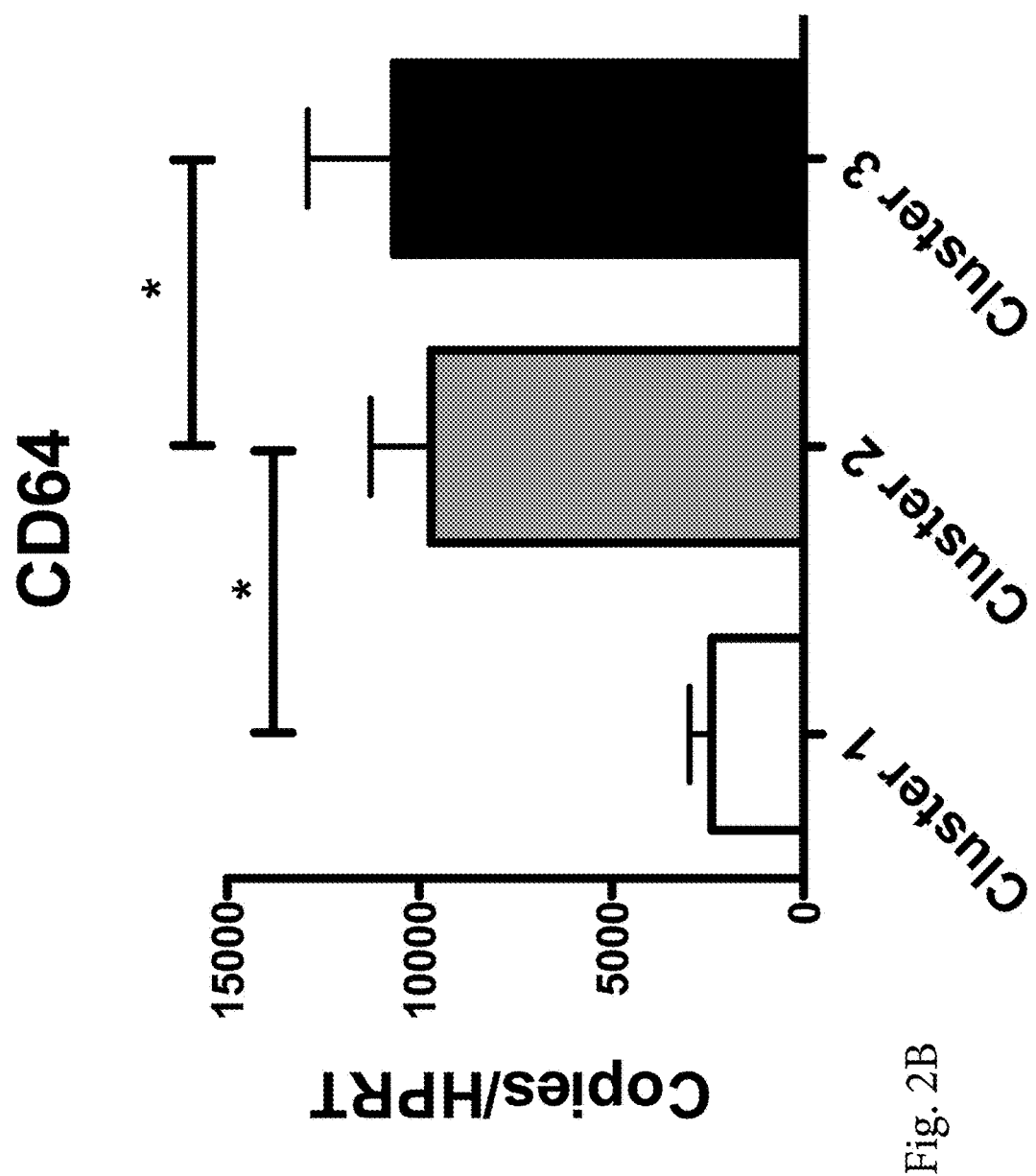
Figure 2C:
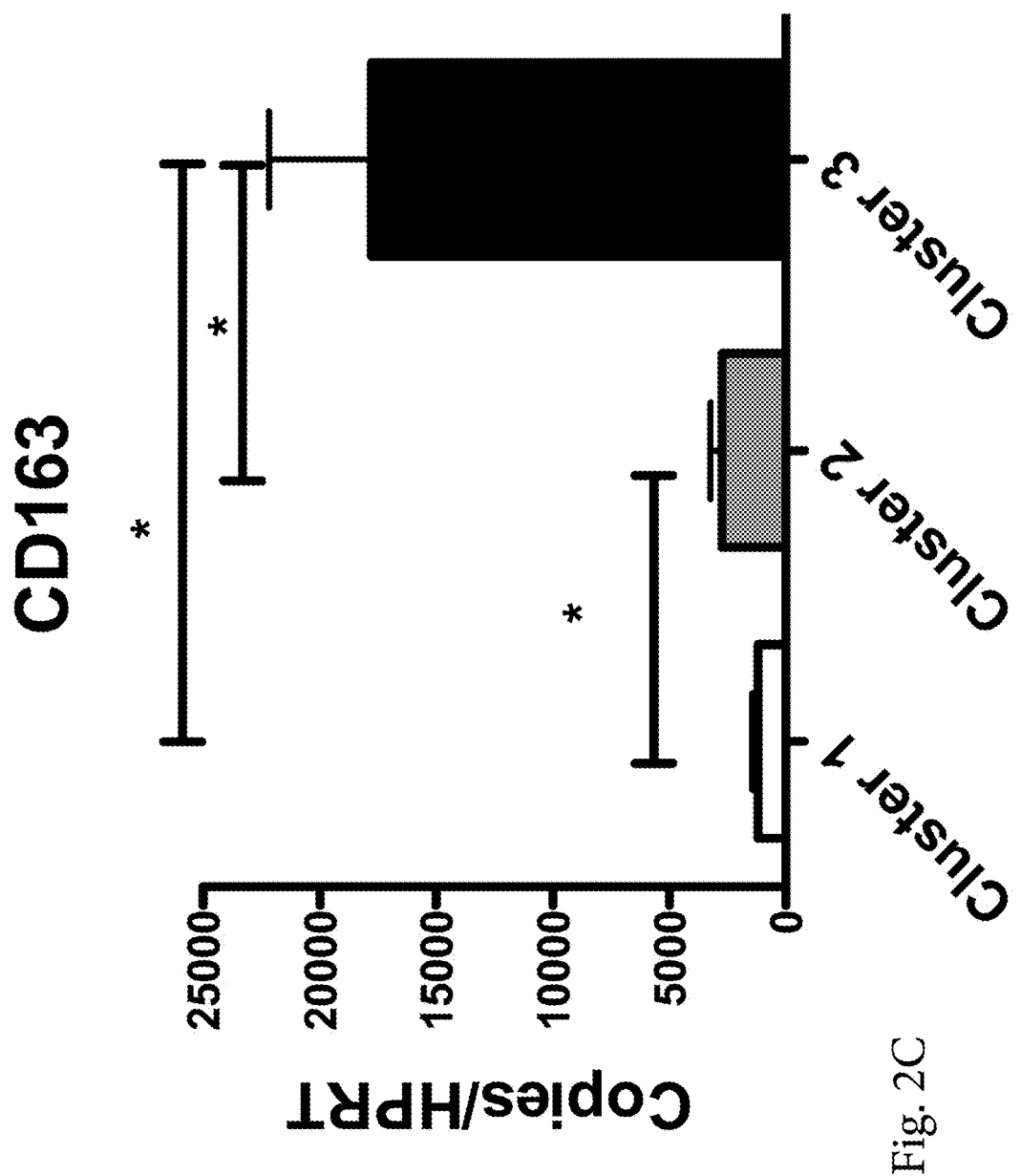
Figure 2D:
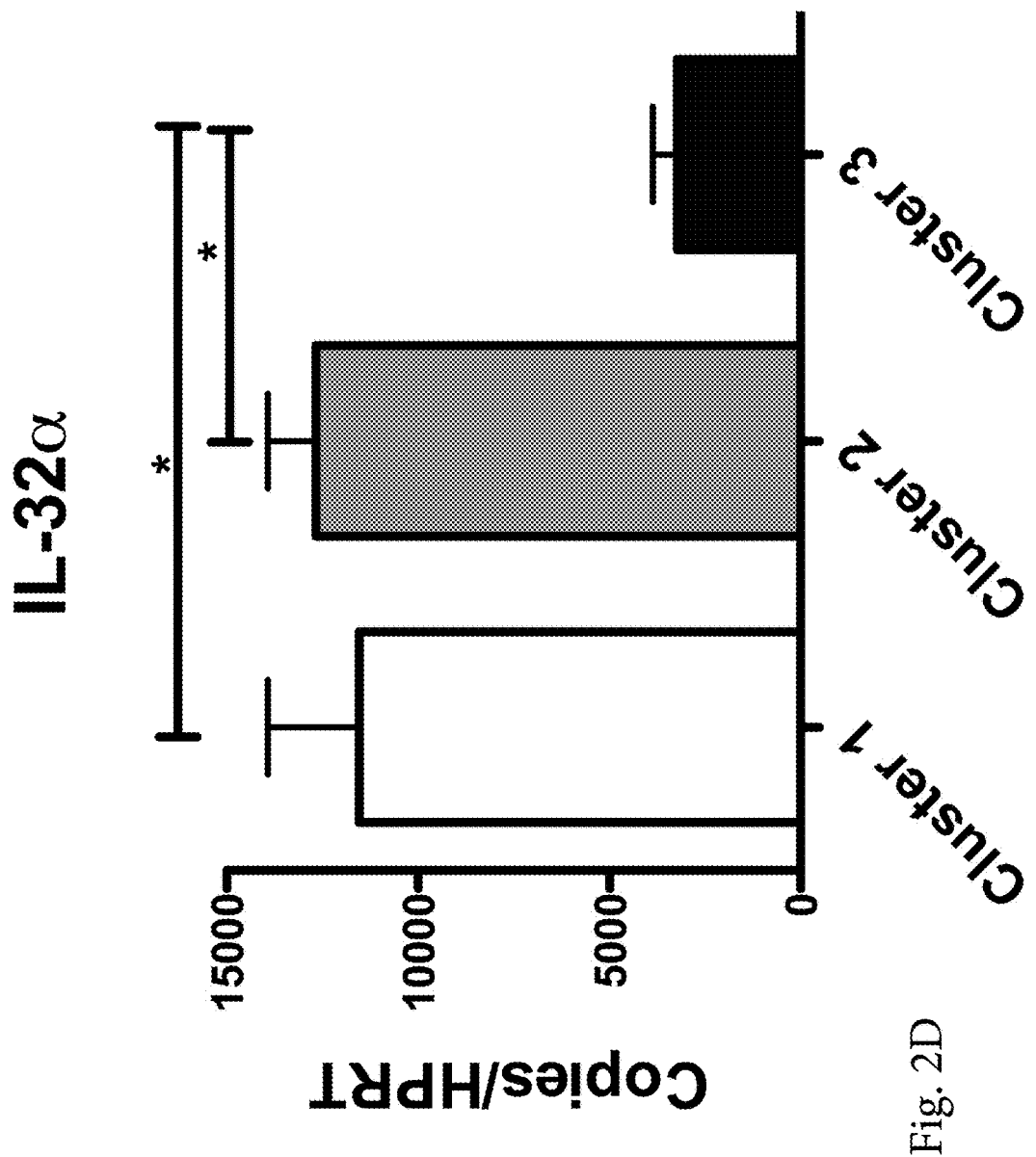
Figure 2E:
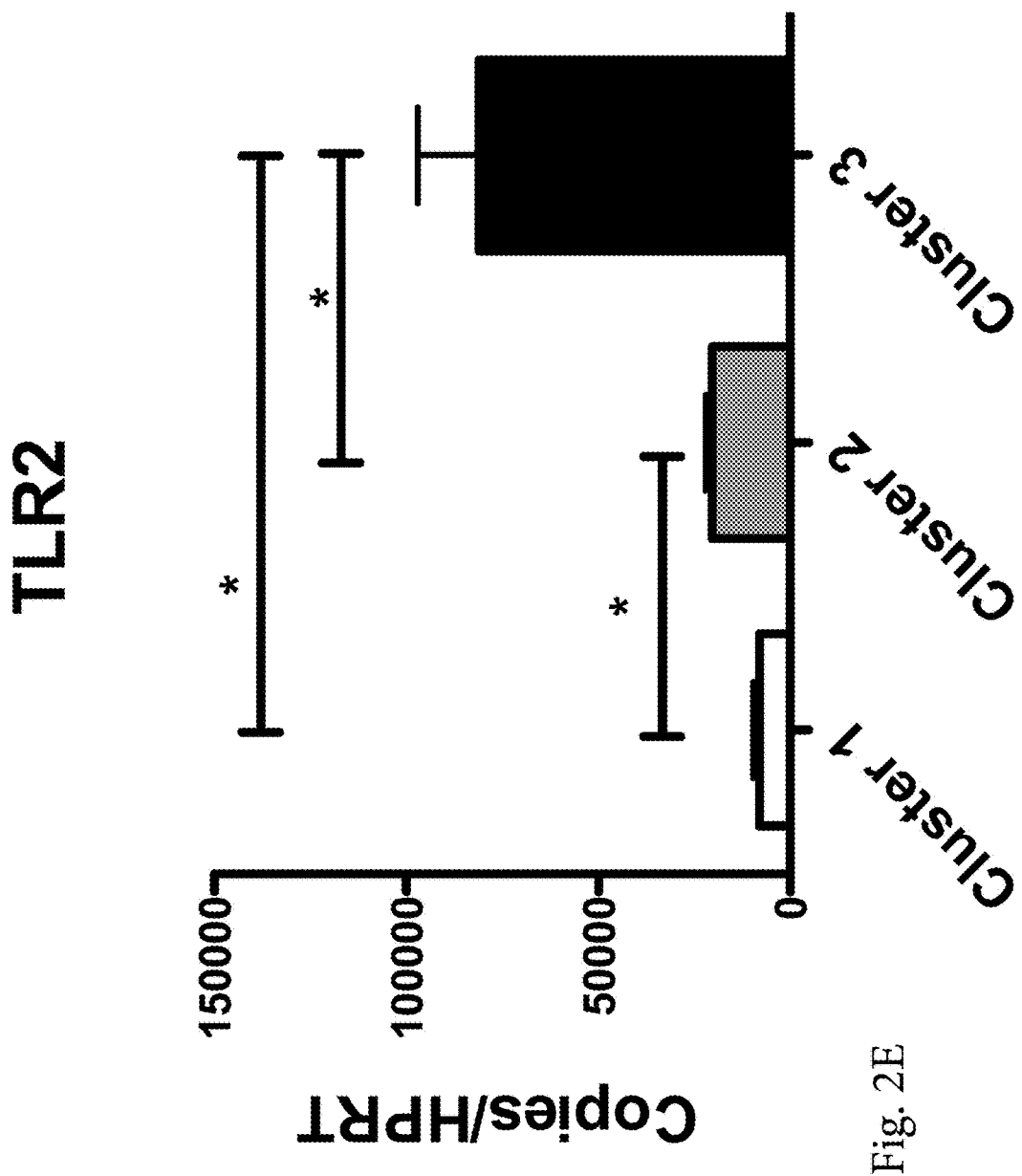
Figure 2F:
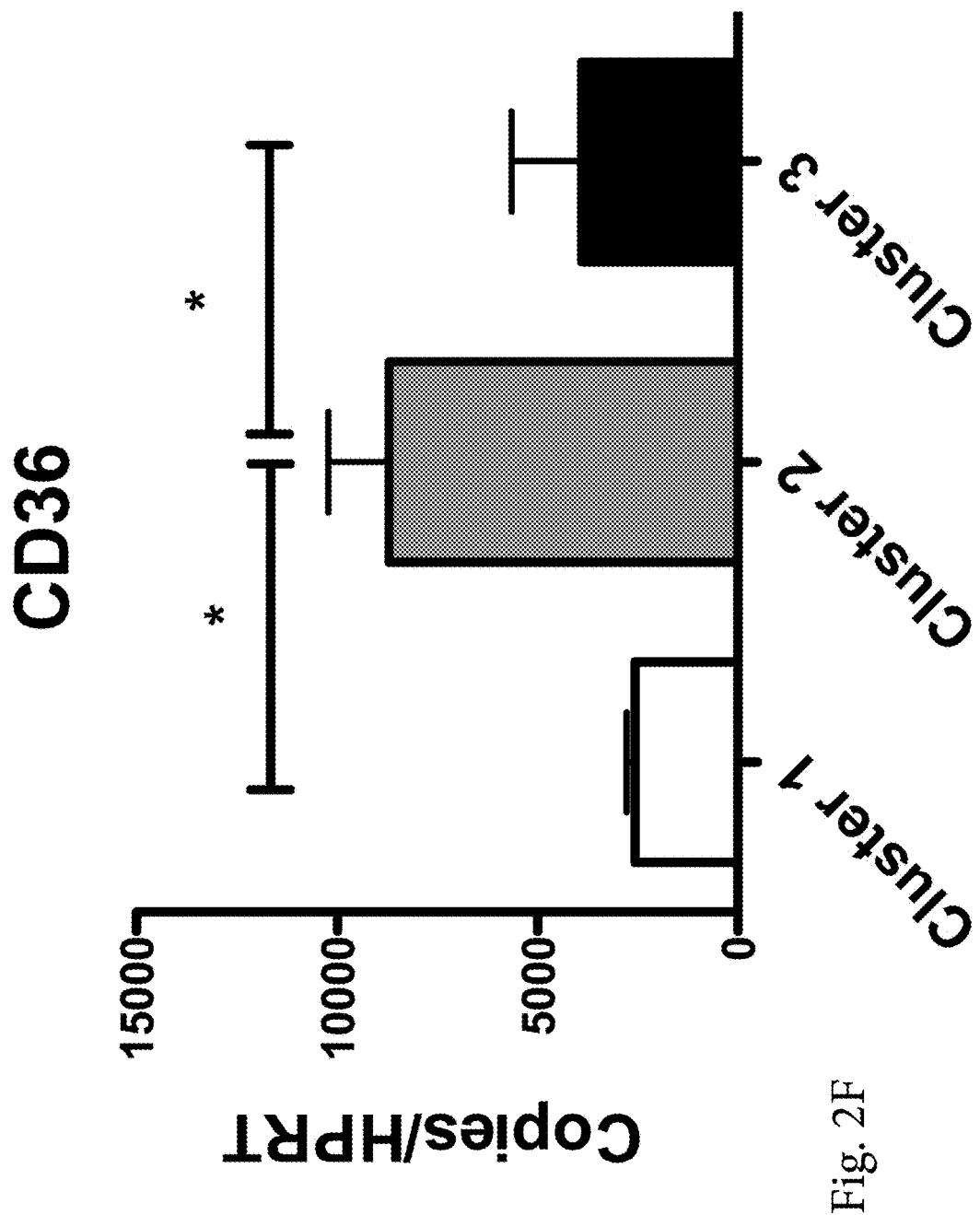
Figure 2G:
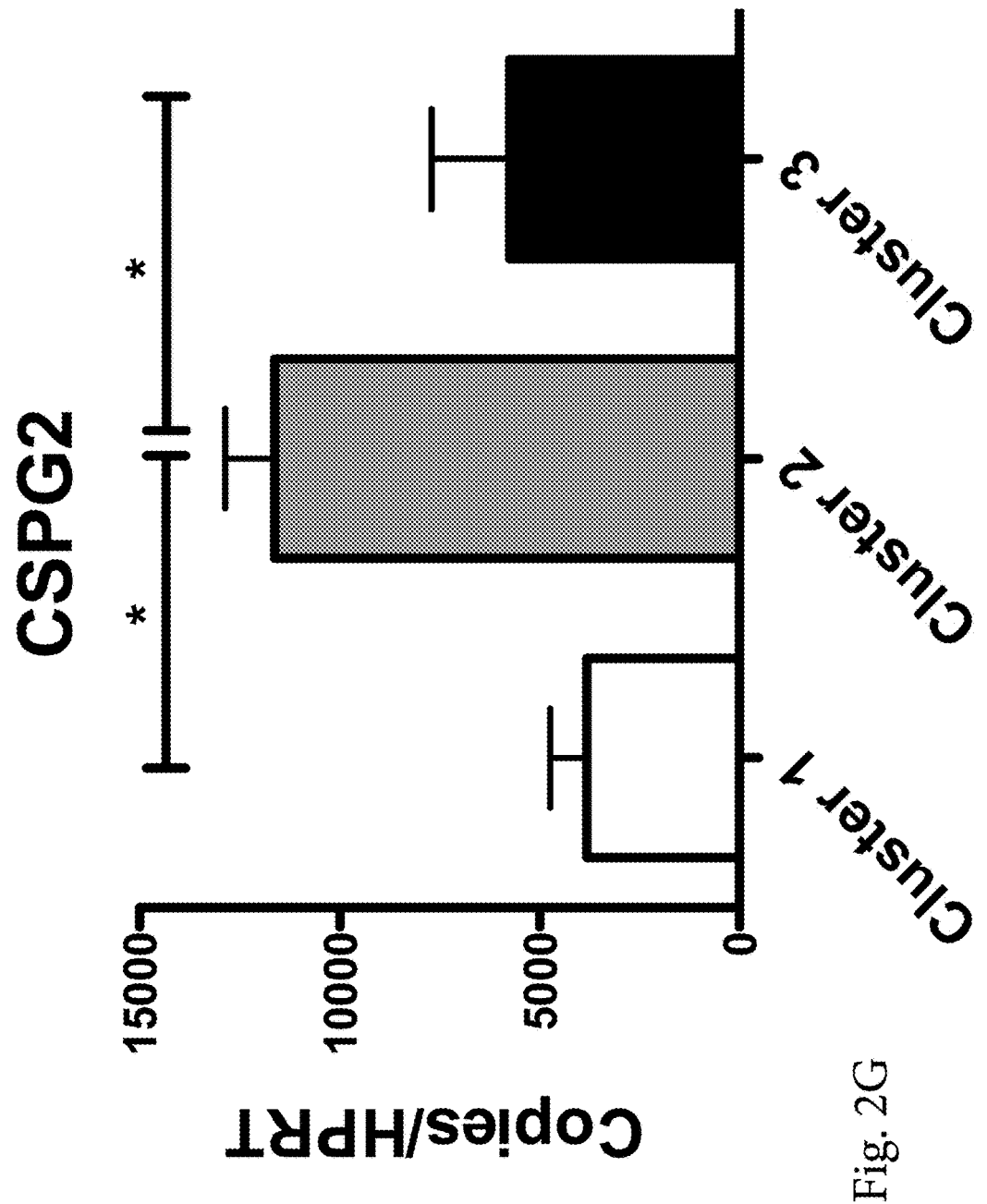
Figure 2H:
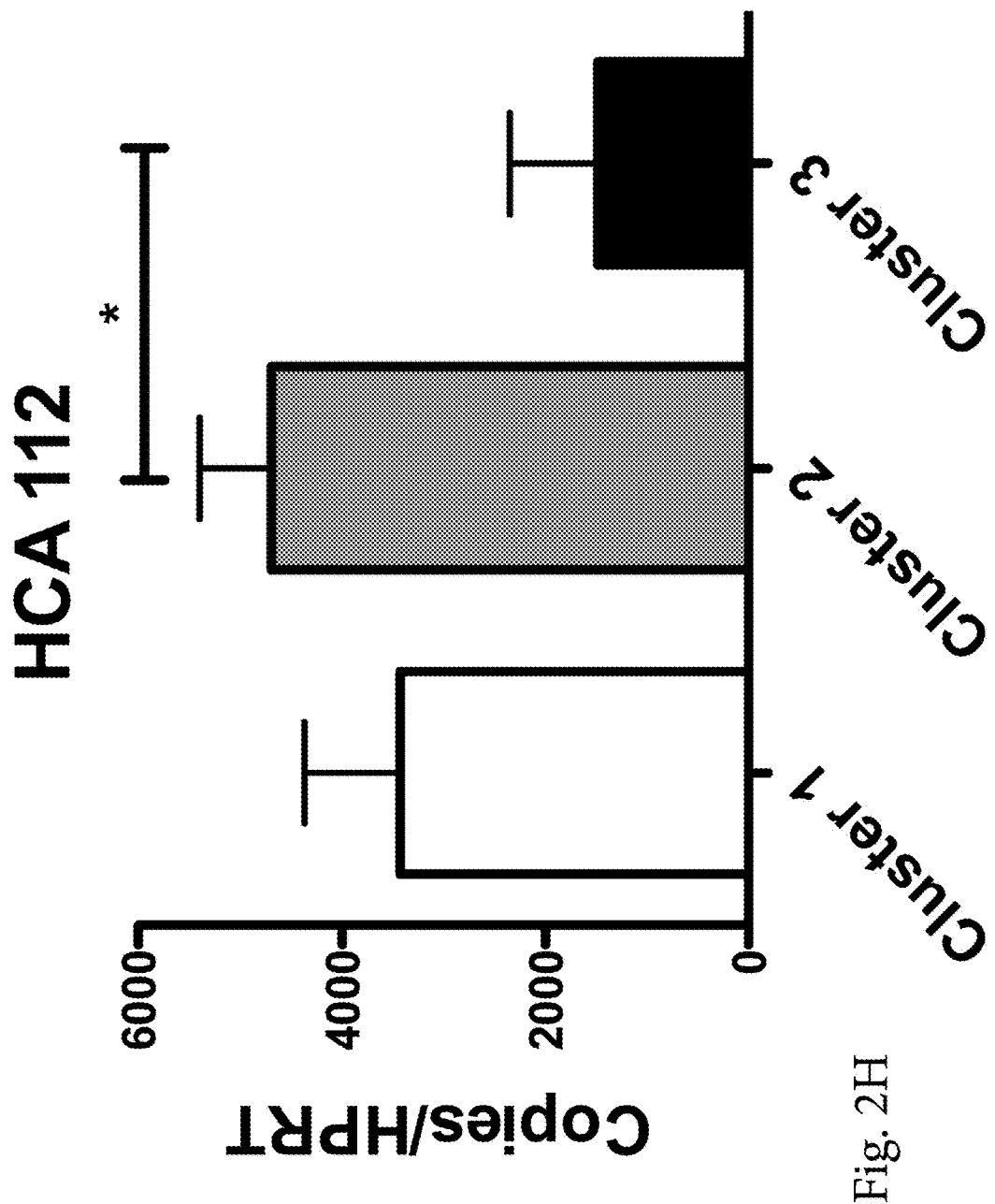
Figure 2I:
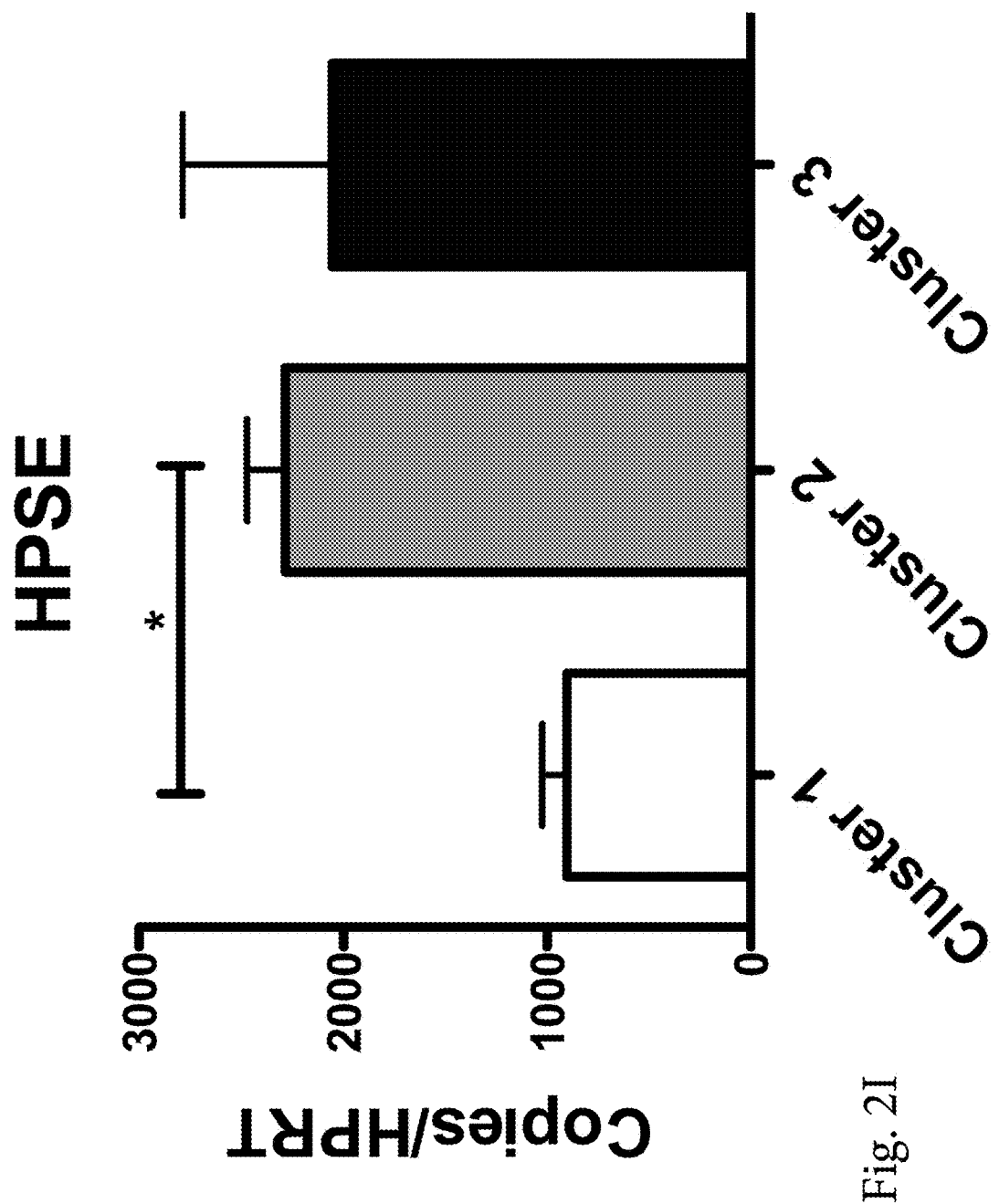
Figure 2J:
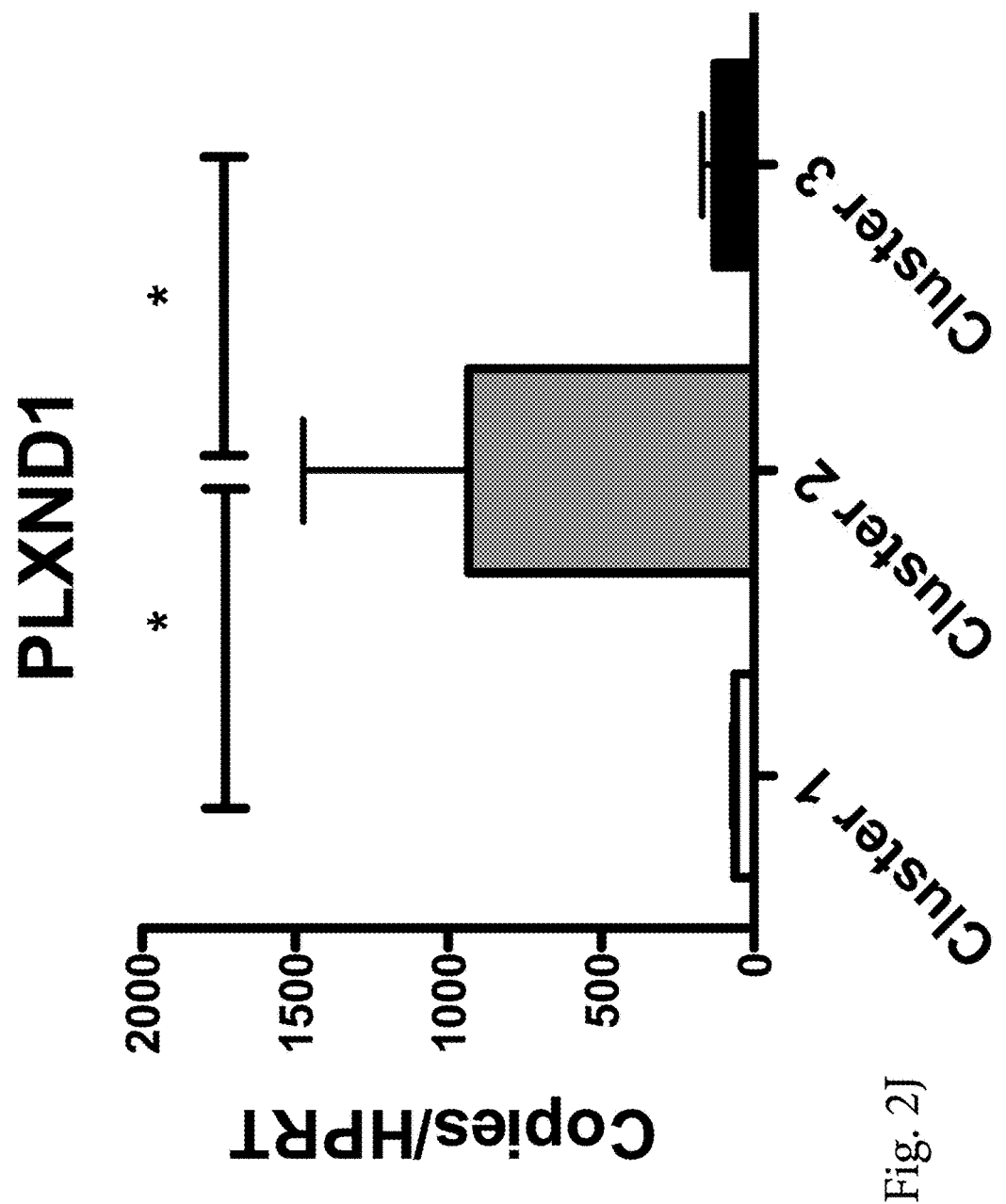

The present invention generally relates to novel methods for categorizing and/or treating subgroups of subjects having an increased risk for increased pulmonary exacerbation and/or disease progression leading to pulmonary decline and in the treatment of a disease that is associated with severe pulmonary exacerbation, such as CF. The invention includes the use of gene biomarkers whose expression patterns correlate with severity degrees of pulmonary exacerbation and pulmonary exacerbation disease progression, including an increased risk of morbidity and/or mortality. The methods of the present invention provide greater sensitivity, specificity and discriminatory capacity than the existing methods that are based on measurements of $FEV_1$ alone and/or CRP (C-reactive protein) alone or in combination and when used in conjunction with measurements of $FEV_1$ and/or CRP to enhance the predictive power of $FEV_1$ and CRP. Spirometry is a common pulmonary function test for measuring lung function. Specifically, $FEV_1$ is the established standard for assessing pulmonary treatment response. When $FEV_1$ measurements are decreased, treatment is initiated. Following two to three weeks of intravenous antibiotic therapy, $FEV_1$ measurements are typically repeated as a quantitative measure of clinical response. Similarly, $FEV_1$ measurements are utilized as the gold standard measurement for treatment response in clinical trials.

The inventors are the first to identify biological pathways underpinning heterogeneity in CF clinical outcomes, in the context of pulmonary exacerbations. Molecular quantification of inflammation has precedence in asthma and chronic obstructive pulmonary disease (COPD) where activation of particular inflammatory pathways corresponds to clinical phenotypes, which differ in terms of underlying inflammation, outcomes, disease progression and response to treatment (Singh D, Fox S M, Tal-Singer R, Bates S, Riley J H, Celli B. Altered gene expression in blood and sputum in COPD frequent exacerbators in the ECLIPSE cohort. PLoS One 2014; 9:e107381; McGrath K W, Icitovic N, Boushey H A, et al. A large subgroup of mild-to-moderate asthma is persistently noneosinophilic. Am J Respir Crit Care Med 2012; 185:612-9; Carolan B J, Sutherland E R. Clinical phenotypes of chronic obstructive pulmonary disease and asthma: recent advances. J Allergy Clin Immunol 2013; 131:627-34; quiz 35). The incorporation of peripheral blood gene signatures adds an additional layer of disease classification beyond the traditional groupings of mild, moderate and severe CF airway disease, based on $FEV_1\%$ predicted. Most strategically, transcriptional classification of disease severity has utility at the time of APE onset, which would allow for health care providers to devise appropriate treatment regimens and follow up for the APE episode and beyond, respectively.

As described herein, the present invention comprises a group of ten genes (CD64, ADAMS, CD36, IL32, HPSE, PLXND1, HCA112, CSPG2, TLR2, and CD163) whose expression patterns were found to correlate with varying degrees of pulmonary exacerbation disease severity. The inventors have determined three clusters or groups in which the expression pattern of the genes fall into that correlate with mild severity, moderate severity or severe severity of pulmonary exacerbation and/or disease progression, including increased morbidity and/or mortality associated with severe pulmonary exacerbation in subjects having lung diseases such as CF. It is noted that these genes are not specific to CF and have varying roles in other conditions characterized by pathologic pulmonary exacerbation and inflammation, including without limitation, asthma, chronic obstructive pulmonary disease, emphysema, interstitial lung disease, bronchitis, acute respiratory distress syndrome and pneumonia (Wu et al., 2008, Am J Respir Crit Care Med 177(7):720-9; Moller et al., 2006, Crit Care Med 34(10): 2561-6).

One embodiment of the present invention relates to a method for categorizing a subject at risk for increased pulmonary exacerbations and/or disease progression. In one aspect, the subject has experienced a pulmonary exacerbation. In one aspect, the method includes obtaining a biological sample from the subject and detecting the expression level of one or more genes selected from TLR2, ADAM9, PLXND1, CD163, CD36, CD64, CSPG2, IL32, HPSE, HCA112 and combinations thereof. The method also includes comparing the expression level of the one or more genes from the subject with gene expression profiles of the same genes known to correlate with increased pulmonary exacerbation and/or disease progression. In one aspect, the method further includes categorizing the subject as at increased risk for increased pulmonary exacerbation and/or disease progression when the subject's gene expression profile correlates to the gene expression profile for increased pulmonary exacerbation and/or disease progression. In one aspect, the biological sample is obtained from the subject at the onset of pulmonary exacerbation.

Another embodiment of the present invention relates to a method to treat a subject at risk for increased pulmonary exacerbation. In one aspect, the subject has experienced a pulmonary exacerbation. In one aspect, the method includes obtaining a biological sample from the subject and detecting the expression level of one or more genes selected from TLR2, ADAM9, PLXND1, CD163, CD36, CD64, CSPG2, IL32, HPSE, HCA112 and combinations thereof. In one aspect, the biological sample is obtained from the subject at the onset of pulmonary exacerbation. The method also includes comparing the expression level of the one or more genes from the subject with gene expression profiles of the same genes known to correlate with increased pulmonary exacerbation and treating the subject aggressively if the subject is at risk for increased pulmonary exacerbation. In one aspect, treating the subject aggressively includes but is not limited to one or more of the following treatments: altering the dosing of the drugs or medication (such as an antibiotic) the subject is being administered for treating pulmonary exacerbation; altering the quantity of antimicrobial agents the subject is being administered; altering the drug(s) selection of the drug(s) the subject has been administered for treating pulmonary exacerbation; changing the antimicrobial agent the subject is being administered; administering an antimicrobial agent to the subject; increasing the duration of drug(s) and/or antimicrobial agent(s) the subject is being administered; lung transplantation; placement on a mechanical ventilator, and/or referral to ICU at a hospital. Subjects determined to be at greater risk for pulmonary exacerbation, such as those determined to be within the most severe cluster group as determined by their gene expression profile, will be treated with more aggressive treatment than subjects in the less severe cluster groups. For example, a subject determined to be in cluster group 3 (severe) as compared to subjects that are determined to be in cluster groups 1 or 2, would have a more aggressive course of treatment (such as lung transplant and/or placement on a mechanical ventilator) than those subjects within cluster groups 1 (mild) or 2 (moderate) as these subjects would be at a greater risk for pulmonary exacerbation and/or death.

In one aspect of the embodiments of the invention described herein, the subject has been diagnosed as having a disease selected from cystic fibrosis, asthma, chronic pulmonary obstructive disease, emphysema, interstitial lung disease, bronchitis, acute respiratory distress syndrome, and pneumonia. In a preferred embodiment, the subject has been diagnosed as having cystic fibrosis.

A patient or subject sample can include any bodily fluid or tissue from a patient that may contain the RNA or protein encoded by the genes contemplated here. The term "sample" or "patient sample" or "subject sample" can be used generally to refer to a sample of any type which contains products that are to be evaluated by the present method, including but not limited to, a sample of isolated cells, a tissue sample and/or a bodily fluid sample. According to the present invention, a sample of isolated cells is a specimen of cells, typically in suspension or separated from connective tissue which may have connected the cells within a tissue in vivo, which have been collected from an organ, tissue or fluid by any suitable method which results in the collection of a suitable number of cells for evaluation by the method of the present invention. The cells in the cell sample are not necessarily of the same type, although purification methods can be used to enrich for the type of cells that are preferably evaluated. Cells can be obtained, for example, by scraping of a tissue, processing of a tissue sample to release individual cells, or isolation from a bodily fluid.

In some aspects, the sample may comprise blood, sputum, bronchoalveolar lavage or urine. In still some aspects the sample may comprise whole blood, Peripheral Blood Mononuclear Cells (PBMCs), leuokocytes, monocytes, lymphocytes, basophils, or eosinophils. In a preferred aspect, the sample is whole blood.

A systemic marker of severe pulmonary exacerbation or increased pulmonary exacerbation disease progression has many advantages, as blood (such as whole blood) can be obtained from subjects of any age and disease severity, and may reflect the status of exacerbation throughout the lung, rather than one segment. This analysis is sensitive, inexpensive, and obtained from blood and/or tissue that is easily accessible in pediatric and adult populations, and has the potential to be performed in a clinical laboratory.

In some aspects, an increased risk of pulmonary exacerbation disease progression includes an increased risk of morbidity and/or mortality and/or exacerbation recurrence. An increase in pulmonary disease progression leads to a shorter interval of exacerbation free time in the subject. Morbidity indicates a need for lung transplant or ICU admission. An increase in morbidity indicates an increase in the subject being referred to lung transplant or having a lung transplant or an increase in the subject being referred to or being admitted to the ICU or being put on mechanical ventilation. As determined by the inventors, the subject's time to the next exacerbation, and/or time to morbidity and/or five year mortality differed significantly between the clusters or groups, particularly between the most divergent clusters or groups, 1 (mild) and 3 (severe). In cluster 1, no subjects needed lung transplants nor died in the follow-up time-period, while 90% of subjects in cluster 3 required ICU transfer for respiratory insufficiency, were referred to transplant, undergone transplant or died over the same time period.

As used herein, the term "expression", when used in connection with detecting the expression of a gene, can refer to detecting transcription of the gene (i.e., detecting mRNA levels) and/or to detecting translation of the gene (detecting the protein produced). To detect expression of a gene refers to the act of actively determining whether a gene is expressed or not and the level at which it expresses. This can include determining whether the gene expression is upregulated or downregulated as compared to a control or as compared to prior to administration of treatment in the same subject or as compared to gene expression profiles of the same genes known to correlate with mild, moderate or severe pulmonary exacerbation disease progression and/or pulmonary exacerbation; or unchanged as compared to a control or as compared to prior to administration of treatment in the same subject or as compared to gene expression profiles of the same genes known to correlate with mild, moderate or severe pulmonary exacerbation disease progression and/or pulmonary exacerbation. Therefore, the step of detecting expression does not require that expression of the gene actually is upregulated or downregulated, but rather, can also include detecting that the expression of the gene has not changed (i.e., detecting no expression of the gene or no change in expression of the gene). When comparing expression levels of genes from the subject with expression levels of the same genes known to correlate with mild, moderate or severe pulmonary exacerbation disease progression and/or pulmonary exacerbation, the known gene expression levels can be from expression levels that have been previously established from populations of subjects that have been previously identified has having mild, moderate or severe pulmonary exacerbation disease progression and/or pulmonary exacerbation. In one aspect, the expression level of at least one, at least two, at least three, at least four, at least five, at least six, at least seven, at least eight, at least nine or all ten of the following genes TLR2, ADAM9, PLXND1, CD163, CD36, CD64, CSPG2, IL32, HPSE, HCA112 is compared. When comparing the expression level of one or more of the genes, to known expression levels, it is to be understood that the comparison is to the same genes.

As used herein, reference to a control, means a subject (or population of subjects) who is a relevant control to the subject being evaluated by the methods of the present invention. The control can be matched in one or more characteristics to the subject, including but not limited to gender, age and disease severity.

Expression of transcripts and/or proteins is measured by any of a variety of known methods in the art. For RNA expression, methods include but are not limited to: extraction of cellular mRNA and Northern blotting using labeled probes that hybridize to transcripts encoding all or part of the gene; amplification of mRNA using gene-specific primers, polymerase chain reaction (PCR), quantitative PCR and reverse transcriptase-polymerase chain reaction (RT-PCR), and/or followed by quantitative detection of the product by any of a variety of means; extraction of total RNA from the cells, which is then labeled and used to probe cDNAs or oligonucleotides encoding the gene on any of a variety of surfaces; in situ hybridization; flow cytometry and detection of a reporter gene. In a preferred aspect, the expression level of the one or more genes is detected by quantitative PCR.

Methods to measure protein expression levels generally include, but are not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), and flow cytometry, as well as assays based on a property of the protein including but not limited to enzymatic activity or interaction with other protein partners. Binding assays are also well known in the art. For example, a BIAcore machine can be used to determine the binding constant of a complex between two proteins. The dissociation constant for the complex can be determined by monitoring changes in the refractive index with respect to time as buffer is passed over the chip (O'Shannessy et al., 1993, *Anal. Biochem.* 212:457; Schuster et al., 1993, *Nature* 365:343). Other suitable assays for measuring the binding of one protein to another include, for example, immunoassays such as enzyme linked immunoabsorbent assays (ELISA) and radioimmunoassays (RIA); or determination of binding by monitoring the change in the spectroscopic or optical properties of the proteins through fluorescence, UV absorption, circular dichroism, or nuclear magnetic resonance (NMR).

In one aspect of the embodiments of the invention described herein, the expression level of each of the following ten genes from the subject, TLR2, ADAM9, PLXND1, CD163, CD36, CD64, CSPG2, IL32, HPSE, and HCA112, is detected and compared. In other aspects of the embodiments of the invention, at least two of the genes, at least three of the genes, at least four of the genes, at least five of the genes, at least six of the genes, at least seven of the genes, at least eight of the genes or at least nine of the genes selected from TLR2, ADAM2, PLXND1, CD163, CD36, CD64, CSPG2, IL32, HPSE, and HCA112 are detected and compared.

In one aspect of any of the embodiments of the invention described herein, the present invention further comprises measuring $FEV_1$ and/or CRP levels in the subject.

Another embodiment of the present invention relates to a kit for detecting the expression of one or more genes selected from CD64, ADAMS, CD36, IL32, HPSE, PLXND1, HCA112, CSPG2, TLR2, and CD163. In one aspect, the kit comprises a detection agent for detecting the expression one or more of the genes. In one aspect, the kit comprises an agent for detecting mRNA expression of one or more of the genes. In still another aspect, the kit comprises an agent for detecting protein expression of one or more of the genes.

As described in the examples below, using unsupervised analysis, the gene expression data identifies and categorizes clusters or groups with significant differences in disease characteristics and underlying inflammation. Exacerbation scores, numbers of pathogenic species infecting patients, and time until next exacerbation were all significantly different for the "severe" cluster (group 3) compared to the "mild" cluster (group 1), in both unadjusted and adjusted models for age, cell counts, and $FEV_1$. The ability of gene variables to discriminate clinically distinct patient groups provides validity to their significance. Leukocyte gene expression can discern inflammatory differences between groups in a manner which is not achievable using standard measures of lung function or inflammation, since $FEV_1$% predicted, white blood cell count and CRP did not differ between clusters. Of great interest, the clusters identify and categorize patients with variable patterns of systemic inflammation, based on leukocyte differentials. Subjects with longer disease free intervals manifest more lymphocytic predominance in the peripheral blood at the onset of exacerbation, while those who go on to exacerbate at shorter intervals are predominantly more neutrophilic. To address the impact of these differences on cluster membership, adjustments were made for cell counts. Nonetheless, the transcripts maintained their significance to identify differences between clusters, indicating that underlying differences in transcription, and not solely cell numbers, exist between groups. The inventors examined the relationship between clusters and 5 year morbidity and survival. While $FEV_1$ had a significant association with mortality, gene expression also defined differences in survival, as seen between clusters 2 and 3. Furthermore, the validation analysis demonstrated that cluster membership based on gene expression could accurately predict morbidity and mortality in a separate cohort, despite different mean $FEV_1$ values in the validation cohort.

Gene differences allow clinicians to distinguish pathobiologic differences between patients with APE. The top gene responsible for differences in cluster membership was TLR2, whose strong signal in the sickest subjects is clearly highlighted in the heat map presented in FIG. 6. The most highly represented genes in the sickest cluster closely link to pathways of microbial recognition. Thus, the TLR2 receptor binds both gram-negative and gram-positive bacterial muropeptides, as a primary line of host defense (Johnson C M, Tapping R I. Microbial products stimulate human Toll-like receptor 2 expression through histone modification surrounding a proximal NF-kappaB-binding site. J Biol Chem 2007; 282:31197-205; Muller-Anstett M A, Muller P, Albrecht T, et al. Staphylococcal peptidoglycan co-localizes with Nod2 and TLR2 and activates innate immune response via both receptors in primary murine keratinocytes. PLoS One 2010; 5:e13153). CD163, a monocyte/macrophage scavenger receptor, dually binds both gram negative and gram positive bacteria (in comparison to TLR2 binding of microbial products) to induce pro-inflammatory cytokine responses (Fabriek B O, van Bruggen R, Deng D M, et al. The macrophage scavenger receptor CD163 functions as an innate immune sensor for bacteria. Blood 2009; 113:887-92). CD64 enacts neutrophil and macrophage phagocytic host defense, once microbial surface ligands contact the CD64 receptor (Huang Z Y, Hunter S, Chien P, et al. Interaction of two phagocytic host defense systems: Fcgamma receptors and complement receptor 3. J Biol Chem 2011; 286:160-8). And finally, ADAM9, expressed by both neutrophils and monocytes, promotes leukocyte extravasation by degrading extracellular membrane protein, elastin, to assist with ongoing leukocyte recruitment (Roychaudhuri R, Hergrueter A H, Polverino F, et al. ADAM9 Is a Novel Product of Polymorphonuclear Neutrophils: Regulation of Expression and Contributions to Extracellular Matrix Protein Degradation during Acute Lung Injury. J Immunol 2014; 193:2469-82). The link between disease progression and innate immune activation is both transcriptional and translational, since enhanced downstream production of pro-inflammatory proteins was present in the "severe" cluster (group 3), while lacking in IFNγ, which is essential for bacterial clearance (Moser C, Kjaergaard S, Pressler T, Kharazmi A, Koch C, Hoiby N. The immune response to chronic *Pseudomonas aeruginosa* lung infection in cystic fibrosis patients is predominantly of the Th2 type. APMIS 2000; 108:329-35; Brazova J, Sediva A, Pospisilova D, et al. Differential cytokine profile in children with cystic fibrosis. Clin Immunol 2005; 115:210-5). While it is not surprising that seriously ill patients with CF have evidence of excessive innate activation, it is novel that a diversity of responses exists between subjects without significant differences in lung function, that this heterogeneity is quantifiable, and that biological differences in innate activation facilitate prognostication.

Prognostication based on host immune responses has been studied extensively in CF (Wojewodka G, De Sanctis J B, Bernier J, et al. Candidate markers associated with the probability of future pulmonary exacerbations in cystic fibrosis patients. PLoS One 2014; 9:e88567; Liou T G, Adler F R, Keogh R H, et al. Sputum biomarkers and the prediction of clinical outcomes in patients with cystic fibrosis. PLoS One 2012; 7:e42748; Downey D G, Martin S L, Dempster M, et al. The relationship of clinical and inflammatory markers to outcome in stable patients with cystic fibrosis.

Pediatr Pulmonol 2007; 42:216-20). Biomarkers from the blood and sputum have not reproducibly predicted short and longer term outcomes. The longstanding gold standard predictor of survival has been $FEV_1$ (Rosenthal M. Annual assessment spirometry, plethysmography, and gas transfer in cystic fibrosis: do they predict death or transplantation. Pediatr Pulmonol 2008; 43:945-52; Kerem E, Reisman J, Corey M, Canny G J, Levison H. Prediction of mortality in patients with cystic fibrosis. N Engl J Med 1992; 326:1187-91). Not uncommonly, any potential association of biomarkers with CF outcomes, such as survival, may be lost once adjustment occurs for lung function, given its powerful influence on mortality (Moffitt K L, Martin S L, Jones A M, et al. Inflammatory and immunological biomarkers are not related to survival in adults with Cystic Fibrosis. J Cyst Fibros 2014; 13:63-8). However, in clinical practice, $FEV_1$ lacks sensitivity. For example, the "severe" cluster (group 3), with a 90% morbidity and mortality rate at 5 years, had an average $FEV_1$ of 37% predicted. While an $FEV_1$ of <30% had a 2-year mortality of 50% in 1992[28], its 2 year mortality was estimated to be less than 20% as of 2011 (George P M, Banya W, Pareek N, et al. Improved survival at low lung function in cystic fibrosis: cohort study from 1990 to 2007. BMJ 2011; 342:d1008). Thus $FEV_1$ alone would not have predicted the severe cluster's outcomes. Furthermore, $FEV_1$ offers no diagnostic insight into particular inflammatory pathways which may predominate in a particular patient. There are no established guidelines for mild, moderate or severe disease based on $FEV_1$ except to refer a subject to lung transplant once the subject's $FEV_1$ falls below 30% predicted. There have been no blood biomarkers which can reproducibly partition subsets of patients at increased risk for exacerbation recurrence over time. Single studies exist which demonstrate blood biomarkers, such as serum calprotectin, whose levels may predict time until next exacerbation (Gray R D, Imrie M, Boyd A C, Porteous D, Innes J A, Greening A P. Sputum and serum calprotectin are useful biomarkers during CF exacerbation. J Cyst Fibros 2010; 9:193-8). CRP has shown variable effect in its ability to predict time until next exacerbation (Gray R D, Imrie M, Boyd A C, Porteous D, Innes J A, Greening A P. Sputum and serum calprotectin are useful biomarkers during CF exacerbation. J Cyst Fibros 2010; 9:193-8; Sequeiros T M, Jarad N. Factors associated with a shorter time until the next pulmonary exacerbation in adult patients with cystic fibrosis. Chron Respir Dis 2012; 9:9-16). As demonstrated by the inventors herein there were no significant differences in $FEV_1$ or in CRP between the 3 clusters or groupings, despite differences in morbidity and mortality between groups, highlighting the shortcomings of these current standard measures of disease.

In the examples below, gene expression of the gene panel disclosed herein was measured cross-sectionally and not longitudinally. Thus, expression data was not available for multiple exacerbations within the same individual. It is also contemplated herein that expression is be measured at the onset of multiple exacerbations, in concert with $FEV_1$, in order to pinpoint systemic trends in inflammation as disease progresses and the point at which maladaptive immune responses begin to predominate. While the assessment of gene expression at the onset of a single exacerbation gives insight into long term mortality, multiple measurements may also be taken to provide further accuracy in risk prediction. In addition, it is contemplated herein to include bacterial expression analysis to assess virulence factors and their impact on expression along with the cluster analysis disclosed herein. The role of bacterial pathogenicity is critical in better understanding how bacterial antigens influence signaling down innate immune pathways in a manner to induce excessively harmful inflammation in the host. Nevertheless, the fact that the gene expression signature continued to have prognostic value for host response and outcomes, despite a variety of bacterial infections in study subjects, is important in terms of its real world applicability.

Expression of the gene panel disclosed herein is believed to allow for molecular phenotyping in CF, allowing stratification of treatment according to the underlying biology for a particular exacerbation. The stability of cluster delineation was supported by a second independent cohort, with an accuracy of 80-90% in predicting morbidity. It demonstrates that gene expression allows risk prediction for longitudinal health outcomes from peripheral blood draws, can allow more precision both to the development of individually tailored regimens and to strategies for timing of transplant referral.

The following examples are provided for illustrative purposes, and are not intended to limit the scope of the invention as claimed herein. Any variations which occur to the skilled artisan are intended to fall within the scope of the present invention.

EXAMPLES

The examples presented below demonstrate that whole blood mRNA transcripts allow molecular categorization of disease endotypes in CF, providing a tool both for distinguishing and treating subjects who are at increased risk for pulmonary exacerbation and disease progression and mortality, and for eliciting distinct pathobiological mechanisms which underlie diversity in host outcomes.

Methods:

Transcript abundance for a leukocyte 10-gene panel was measured from whole blood, in a cohort of adult CF subjects (n=57) at the beginning and end of treatment for an acute pulmonary exacerbation. A hierarchical cluster analysis was performed on the gene expression data at the beginning of treatment. Clusters were analyzed for differences in $FEV_1$ (% predicted), CRP (log transformed), return to baseline $FEV_1$ at the end of treatment, time to next exacerbation and time to death, transplant, transplant referral or mechanical ventilation. A discriminant analysis was performed in a separate cohort as a validation of the ability of cluster membership to predict future outcomes in a separate population.

Full study design details of the CF circulating mRNA study have previously been reported (Nick J A, Sanders L A, Ickes B, et al. Blood mRNA biomarkers for detection of treatment response in acute pulmonary exacerbations of cystic fibrosis. Thorax 2013; 68:929-37). The study was a 3-year (2008-2011), single center, prospective observational study of 57 CF subjects, over the age of 18, suffering from APE. Diagnosis of exacerbation was based on the Cystic Fibrosis Foundation defined clinical practice guidelines (Foundation C F. Microbiology and infectious diseases in cystic fibrosis: V (Section 1). Bethesda, Md.; 1994), and all subjects underwent calculation of an exacerbation score to confirm presence of exacerbation (Rosenfeld M, Emerson J, Williams-Warren J, et al. Defining a pulmonary exacerbation in cystic fibrosis. J Pediatr 2001; 139:359-6). Subjects were deemed eligible regardless of pathogen, disease severity or mutation. Study enrollment had no impact on treatment interventions. All enrolled subjects continued to receive APE therapy as directed by their physician. Data were collected at the initiation and conclusion of treatment of APE.

In all enrolled subjects, transcript abundance was quantified by quantitative PCR (qPCR) in pre and post antibiotic samples, for the following ten genes: CD36, CD64, CD163, toll-like receptor 2 (TLR2), plexin D1 (PLXND1), hepatocellular carcinoma associated antigen 112 (HCA112), heparanase (HPSE), a disintegrin and metalloproteinase domain 9 (ADAM9), versican (CSPG2), and IL-32 (Nick J A, Sanders L A, Ickes B, et al. Blood mRNA biomarkers for detection of treatment response in acute pulmonary exacerbations of cystic fibrosis. Thorax 2013; 68:929-37). All subjects who had transcripts analyzed underwent simultaneous phlebotomy for serum. Serum samples were frozen at −80° C. and later underwent ELISA analysis for IL-1b, IL-6 and IFNg proteins (Mesoscale, Rockville, Md.).

Cluster analysis of transcript abundance was performed via a hierarchical clustering algorithm based on Euclidean distances, using the Ward minimum variance method, such that within-cluster variation was minimized (Brazova J, Sediva A, Pospisilova D, et al. Differential cytokine profile in children with cystic fibrosis. Clin Immunol 2005; 115: 210-5). Dendrograms were produced and visually determined separation between clusters. To compare differences among clusters, ANOVA and Fisher's exact tests were used for continuous and categorical variables, respectively. Linear regression models were used to allow for the addition of cell count covariates, including neutrophil, lymphocyte, and monocyte counts across clusters.

Kaplan Meier analyses were used for time to event outcomes of interest. Log rank tests were employed to determine differences between clusters in the Kaplan Meier analyses. Age and $FEV_1$ adjusted time to event analyses were modeled with Cox proportional hazards regressions. When overall tests were significant, pairwise differences were examined for significance. Neutrophil, lymphocyte and monocyte cell counts were considered in models, and backwards eliminated performed based on a significant p-value cutoff of 0.15. Cell count percentages were also considered but did not significantly differ from raw cell counts.

A linear discriminant analysis based on equal variances between clusters was performed on an independent cohort of ten subjects who were not included in the training set. Prior probabilities were set to be proportional to cluster size. Posterior probabilities of membership into clusters designated in the training set were calculated for the test set, for time until next exacerbation and time until morbidity/mortality event (transplant, transplant referral, ICU admission or death). In addition, a linear discriminant analysis was also performed on the original 57 subjects, where 70% of the subjects were randomly selected for the training set, and the remaining 30% were selected for the testing set. All tests were 2-tailed with an alpha level of 0.05. All analyses were conducted with SAS version 9.3 (SAS Institute Inc, Cary, N.C.).

Overall Results of the Examples Presented Below:

CF host transcript abundance reflects variability in immune responses to standard treatment algorithms for CF exacerbations. At the initiation of exacerbation therapy, 3 distinct subject clusters were identified. $FEV_1$, CRP (log transformed) and return to baseline $FEV_1$ following treatment were not different between clusters. However, time to next exacerbation p<0.0001), and time to morbidity (lung transplant referral or ICU admission) and 5 year mortality differed significantly between clusters (p=0.0002), particularly between the most divergent clusters, 1 (mild) and 3 (severe). In cluster 1, no subjects have been transplanted nor have died in follow-up, while 90% of subjects in cluster 3 required ICU transfer for respiratory insufficiency, have been referred to transplant, have undergone transplant or have died over this time period (p=0.0001). Six genes as noted in Example 1 below were significant in determining cluster membership between groups 1 and 3 (p<0.05 for all genes).

Example 1

Cluster Analysis Resulted in Categorization of Exacerbation Samples into Three Subgroups of Subjects Based on Gene Expression Three distinct clusters were partitioned and categorized from the data, based on a fixed semi-partial R squared distance of approximately 0.075 between clusters (FIG. 1). Cluster groups were comprised of sample sizes of n=10 (Cluster 1/mild), n=37 (Cluster 2 /moderate), and n=10 (Cluster 3/severe). Subjects in cluster 1 were distinguished by significantly lower expression of ADAM9, CD163, and TLR2 compared to those in both clusters 2 and 3 (FIG. 2). The greatest magnitudes of expression differences were seen between Clusters 1 and 3. Cluster 1 expression of ADAM9, CD64, CD163, IL32, HCA112 and TLR2 was significantly different from those subjects in cluster 3. Rank of importance was calculated for the genes which most highly determined cluster membership or category, with the following rank in descending order (with accompanying F statistic from the ANOVA test): 1. TLR2 (45.77), 2. ADAM9 (31.85), 3. PLXND1 (21.31), 4. CD163 (19.55), 5. CD36 (16.09), 6. CD64 (14.98), 7. CSPG2, 8. IL32(11.7), 9. HPSE (9.61), and 10. HCA112 (6.17).

The test cohort included 57 adult subjects who underwent hierarchical clustering based on gene expression at the onset of pulmonary exacerbations. Demographic data and sample sizes of the three identified clusters as well as cluster-specific clinical outcomes are shown in Table 1. Clusters are labeled 1, 2, and 3, or, mild, moderate and severe respectively (based on clinical outcomes). There were no significant differences between age, diabetic status, $FEV_1$% predicted, or DF508 homozygote status between the three clusters. In addition, the return to the previous year's baseline $FEV_1$ following exacerbation treatment did not differ significantly between clusters. Cluster 3 had significantly higher exacerbation scores, more co-infections identified from respiratory cultures, and a non-significant trend towards lower lung function. Characteristics of the validation cohort are described in Example 5.

TABLE 1

Characteristics of study clusters

| | Cluster 1 | Cluster 2 | Cluster 3 | p value |
|---|---|---|---|---|
| No. of subjects | 10 | 37 | 10 | |
| Age (mean +/− SD) years | 30 ± 11 | 32 ± 10 | 28 ± 7 | 0.42 |
| Gender- no. (% female) | 7 (70) | 25 (68) | 4 (40) | 0.29 |

TABLE 1-continued

Characteristics of study clusters

| | Cluster 1 | Cluster 2 | Cluster 3 | p value |
|---|---|---|---|---|
| Genotype no. (%) | | | | |
| ΔF508/ΔF508 (%) | 5 (50) | 21 (57) | 4 (40) | 0.64$ |
| Other (%) | 5 (50) | 16 (43) | 6 (60) | |
| $FEV_1$ (mean +/− SD % predicted)* | 53 ± 17 | 42 ± 17 | 37 ± 15 | 0.1 |
| Return to ≥90% peak FEV1 from previous year, post-therapy (%)* | 8 (89) | 28 (85) | 7 (78) | 0.86 |
| Exacerbation severity (mean +/− SD Rosenfeld score)~ | 4.52 ± 0.88 | 5.02 ± 1.65 | 6.46 ± 1.07 | 0.009 |
| Sputum culture~ | | | | |
| *Pseudomonas aeruginosa* only (%) | 5 (50) | 15 (41) | 0 | 0.02$ |
| *Pseudomonas aeruginosa* + *Staphylococcus aureus*, or other pathogens (%) | 5 (50) | 22 (59) | 10 (100) | |
| Health care utilization in follow-up | | | | |
| Admissions in subsequent year no. (%)~ | | | | |
| None | 7 (70) | 15 (42) | 0 | 0.003$ |
| 1+ | 3 (30) | 21 (58) | 10 (100) | |
| Admissions to ICU/mechanical ventilation (%) | 0 | 3 (8.1) | 2 (20) | 0.39 |
| Awaiting lung transplant or s/p referral (%)~ | 0 | 8 (21.6) | 8 (80) | <.0001 |
| Lung transplantation (%) | 0 | 5 (13.5) | 1 (10) | 0.82 |
| Death (%) | 0 | 8 (22) | 4 (40) | 0.11 |
| Composite: Death, lung transplantion, or referral to lung transplant** | 0 | 12 (32) | 9 (90) | <.0001 |

$statistic represents comparison of the proportion between the indicated row and the row immediately underneath
*6 subjects missing prior $FEV_1$ data (1 from cluster 1, 4 from cluster 2, and 1 from cluster 3)
~Cluster 1 and 2 significantly different from Cluster 3.
**Statistic calculated as a composite score of 3 variables. Signficant differences found across all three clusters.

Example 2

Figure 3C:
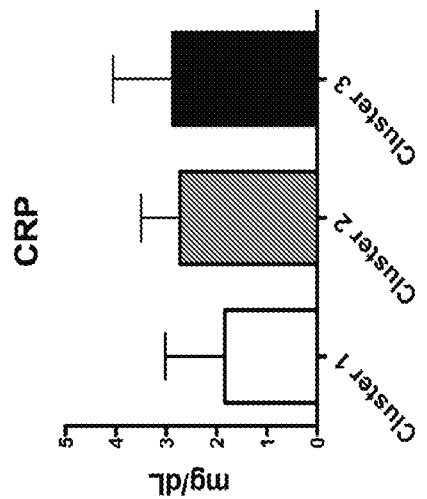
FIGS. 3A to 3C show the clinical variable differences between clusters, specifically white blood cell (WBC) count, $FEV_1$% predicted and CRP. Mean WBC counts ($10^9$/L), $FEV_1$% predicted, and C-reactive protein (CRP) (mg/dL) are demonstrated in column graphs, and error bars represent SEM. Differences between clusters were evaluated with ANOVA, following log-transformation of WBC counts and CRP.
Figure 3B:
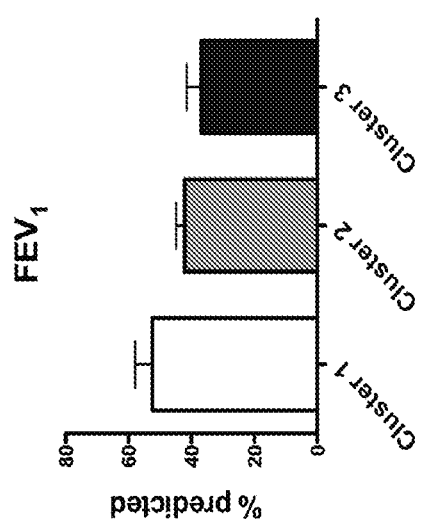
Figure 3A:
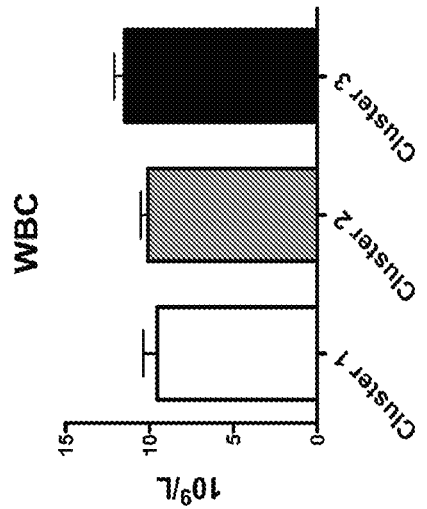

Cluster Assignment and Cross-Sectional Analysis of Systemic Inflammation and Pulmonary Function Column graphs in FIG. 3 reflect variations in standard measures of inflammation between the cluster subgroups. WBC and CRP values (both log transformed) were not significantly different between clusters (Bartlett's test for homogeneity of variance across clusters, p=0.73 and 0.89 respectively). Despite a decreasing trend from cluster 1 to cluster 3, $FEV_1$% predicted did not vary significantly between clusters (Bartlett's test for homogeneity of variance, p=0.86). When white blood cell differential counts were compared, neutrophil, lymphocyte and monocyte counts between clusters did differ. Peripheral lymphocyte counts were higher in cluster 1 versus 3 (p=0.0008) and cluster 1 versus 2 (p=0.0008). Peripheral neutrophil percentages were lower in cluster 1 versus 3 (p=0.0008) and cluster 2 versus 3 (p=0.02). No significant differences were found across clusters for peripheral monocyte counts.

Example 3

Cluster Assignment and Short Term Outcomes after Exacerbation

Figure 4:
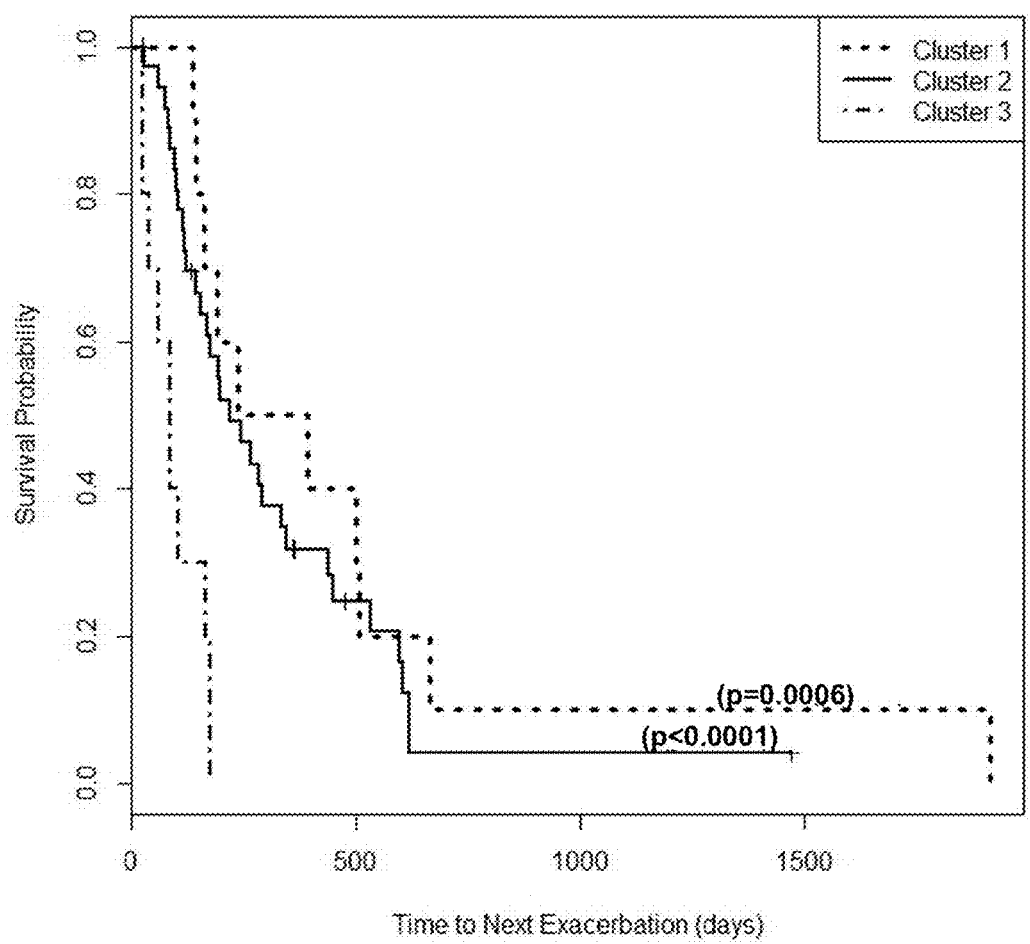
FIG. 4 shows the association between gene expression at APE onset and time until next exacerbation. Kaplan-Meier curves demonstrate differences in time to next exacerbation (in days) between clusters. After adjusting for baseline $FEV_1$, age, and neutrophil cell counts (the last of which remained in the model after backward selection), the difference between clusters in time to exacerbation event remained significant (Cluster 3 versus 1, hazard ratio or HR=3.9, p=0.03; and Cluster 3 versus 2, HR=3.9, p=0.0002). In models with the cluster variable alone, Cluster 3 versus 1 had an HR of 6.6, p=0.0002, and Cluster 3 versus 2 had a HR of 4.7, p=0.0001. The ability of $FEV_1$ alone to predict time to next exacerbation had borderline significance (p=0.05). Adjusted P-values are expressed, for respective clusters, versus cluster 3. Overall p<0.0001.

To determine whether exacerbation outcomes differed between the three clusters, the subjects' return to baseline $FEV_1$ following treatment was evaluated, which was defined as achievement of >90% of best $FEV_1$ in the year prior to study with treatment. There were no differences between clusters in reaching baseline $FEV_1$ following treatment of exacerbation (p=0.86, Fisher's exact test). Persistent systemic inflammation at treatment end, based on abnormally elevated CRP (>0.4 mg/dL), was compared across clusters. Incidence of elevated post-treatment CRP was not significantly different between clusters (p=0.84, Fisher's exact test). However, significant differences in time to subsequent pulmonary exacerbation occurred between clusters. A survival analysis (FIG. 4) revealed that individuals in Clusters 1 and 2 had longer intervals of exacerbation free time, compared to those individuals in cluster 3 (median times for clusters 1, 2 and 3 were 314.5, 218 and 85 days, respectively), and these comparisons were statistically significant (p=0.0006 for Cluster 1 versus 3; p<0.0001 for Cluster 2 versus 3; overall p<0.0001). After adjusting for baseline $FEV_1$, age, and neutrophil cell counts (the last of which remained in the model after backward selection), the differences between clusters in time to exacerbation event remained significant (Cluster 3 versus 1, hazard ratio or HR=3.9, p=0.03; and Cluster 3 versus 2, HR 3.8, p=0.002). In models with the cluster variable alone, Cluster 3 versus 1 had a HR of 6.6, p=0.0002, and Cluster 3 versus 2 had a HR of 4.7, p=0.0001. The ability of $FEV_1$ alone to predict time to next exacerbation had borderline significance (p=0.05).

Example 4

Figure 5:
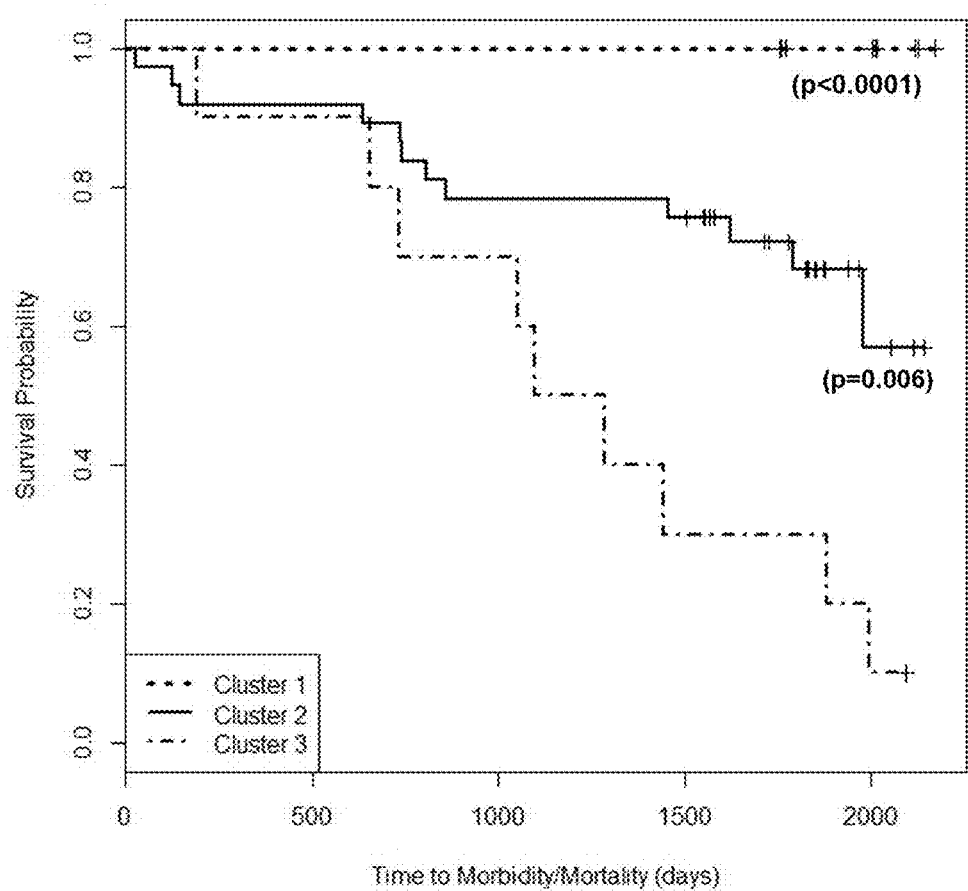
FIG. 5 shows the association between gene expression at APE onset and a composite morbidity and mortality outcome (death, transplant or transplant referral, intensive care unit (ICU) admission for respiratory decline). Kaplan-Meier curves demonstrate differences in adverse disease outcomes between clusters. Adjusted p values are expressed, for respective clusters, versus cluster 3. Overall p=0.0002.

Cluster Assignment and Future Indicators of Disease Progression, Morbidity and Mortality To determine whether cluster membership in a certain category could predict other major events characteristic of disease progression, time to the following was evaluated for subjects within each cluster: mechanical ventilation or ICU admission for pulmonary status (not related to transplant), referral to lung transplantation for end-stage disease (FEV1<30% predicted or loss of treatment response to antibiotics), actual lung transplantation, or death. A survival analysis by the Kaplan-Meier method revealed longer intervals of morbidity and mortality free time for subjects in clusters 1 and 2 compared to cluster 3 (cluster 1 versus 3, p<0.0001; cluster 2 versus 3, p=0.006; overall p=0.0002; median survival times not estimable for clusters 1 and 2 due to no or few events in these clusters) (FIG. 5). CF subjects whose gene expression fell within Cluster 1 had a 0% rate of significant events (increase in morbidity, or mortality), while CF subjects whose gene expression fell within Cluster 3 had a 90% rate of major events (p=0.0001, Fisher's exact test). Cox proportional hazards regression was used to adjust for the effect of differences in baseline $FEV_1$, age and monocyte cell counts (which remained in the model after backwards selection) on survival. Unadjusted p values rose following adjustment, primarily due to $FEV_1$ effect on survival. Yet, significant differences remained between clusters 2 and 3 (HR=5, p=0.004; compared with HR=3.2, p=0.009 for the model with cluster variable alone), in long term survival and morbidity based on gene expression. Hazard ratios for cluster 1 could not be computed since no events occurred in that group. $FEV_1$ alone was a predictor of major events (p=0.005).

Example 5

Validation of Cluster Categories

As a validation, a linear discriminant analysis was performed for the gene predictors and their ability to predict increased morbidity and mortality, as defined above, in a separate population (n=10). The comparison demographics for both training and test cohorts are shown in Table 2. The validation cohort overall was healthier, based on higher pre- and post-APE treatment $FEV_1$% predicted. The group also had not suffered any morbidity or mortality events as defined above at 2 years follow-up. Two separate validation approaches were taken. First, a discriminant analysis of 57 subjects from the original dataset was utilized to predict morbidity and mortality in the validation dataset of 10 additional subjects. Even though the mean $FEV_1$ was higher for validation subjects than for the main study subjects (p<0.05), the probability of genes to predict significant morbidity or mortality events was 90%. A second validation approach was performed where a training and test dataset were created from the 57 original subjects, randomly splitting them into 2 groups. A 3:1 ratio was used in the allocation, yielding 40 subjects to fit the model and 17 for validation. In this analysis, genes discerned morbidity and mortality with an 82% probability.

TABLE 2

CHARACTERISTICS OF STUDY COHORTS

| | Training cohort | Test cohort | P-value |
|---|---|---|---|
| No. of subjects | 57 | 10 | |
| Age in years, mean ± SD^ | 31 ± 10 | 34 ± 17 | 0.52 |
| Gender - no. female (%) | 36 (63) | 6 (60) | 1.00 |
| Genotype - no. ΔF508/ΔF508 (%) | 30 (53) | 4 (40) | 0.51 |
| $FEV_1$ % of predicted, mean ± SD | | | |
| Pre | 43 ± 17 | 62 ± 22 | 0.02 |
| Post | 53 ± 18 | 74 ± 20 | 0.01 |
| Difference (Post − Pre) | 10 ± 9 | 11 ± 7 | 0.49 |
| Return to > 90% peak $FEV_1$ from previous year* | 43 (84) | 8 (80) | 0.66 |
| Exacerbation severity (mean Rosenfeld score)^ | 5.2 ± 1.6 | 5.9 ± 1.3 | 0.13 |
| Sputum culture - no. (%) | | | 0.48 |
| *Pseudomonas aeruginosa* only | 20 (35) | 5 (50) | |
| *P. aeruginosa* + *S. aureus*, or other pathogens (%) | 37 (65) | 5 (50) | |
| Health care utilization in follow-up | | | |
| Admissions in subsequent year no. (%) | | | 1.00 |
| None | 22 (39) | 4 (40) | |
| 1+ | 34 (60) | 6 (60) | |
| Admissions to ICU/mechanical ventilation | 5 (8.9) | 0 | 1.00 |
| Referral to lung transplant | 16 (29) | 0 | 0.10 |
| Lung transplantation | 6 (11) | 0 | 0.58 |
| Death | 13 (24) | 0 | 0.19 |

^P-value from 2 sample t-test assuming unequal variances. Otherwise, p-value from Fisher's exact test.
*From n = 51 subjects who had previous year's $FEV_1$ available

Example 6

Figure 6:
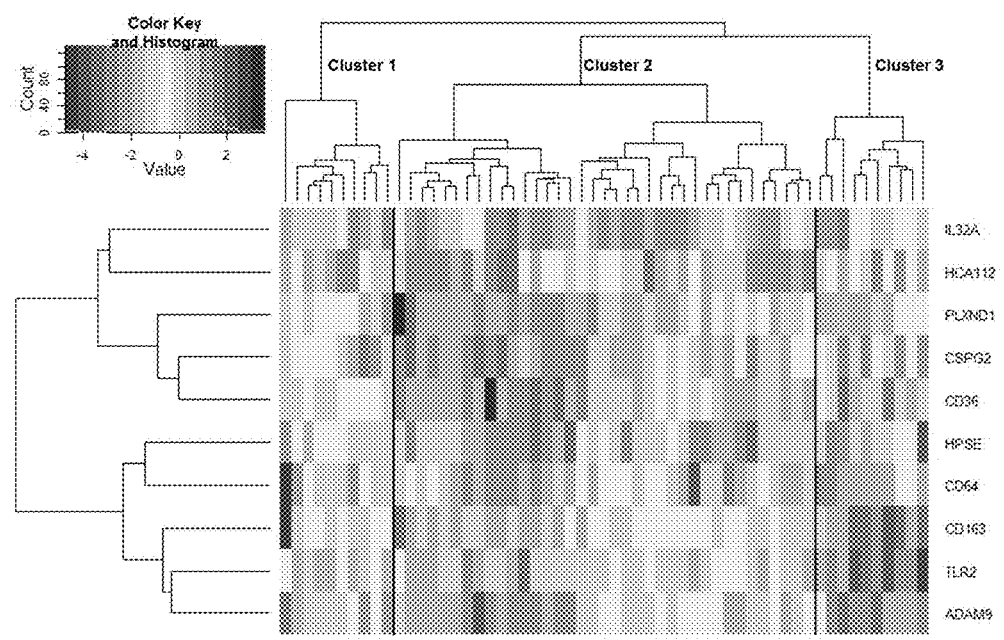
FIG. 6 shows a heat map representing differential expression of genes between clusters. Expression of single genes (rows) for each subject within the 3 clusters (columns) are depicted with a grey-scale color-coded histogram representing over- and under-expression for each gene. Shades on the left side of the color key signifies reduced gene expression, while shades on the right side of the color key indicate increased expression.

Distinct Biological Pathways Specific to Exacerbations and Association of Gene Expression with Downstream Pro-Inflammatory Proteins A heat map was generated to depict gene differences between clusters (FIG. 6). Since the TLR2 gene most highly influenced cluster membership, from the 10 gene panel, subjects within clusters were tested for evidence of downstream differences in protein expression related to inflammation.

Figure 7B:
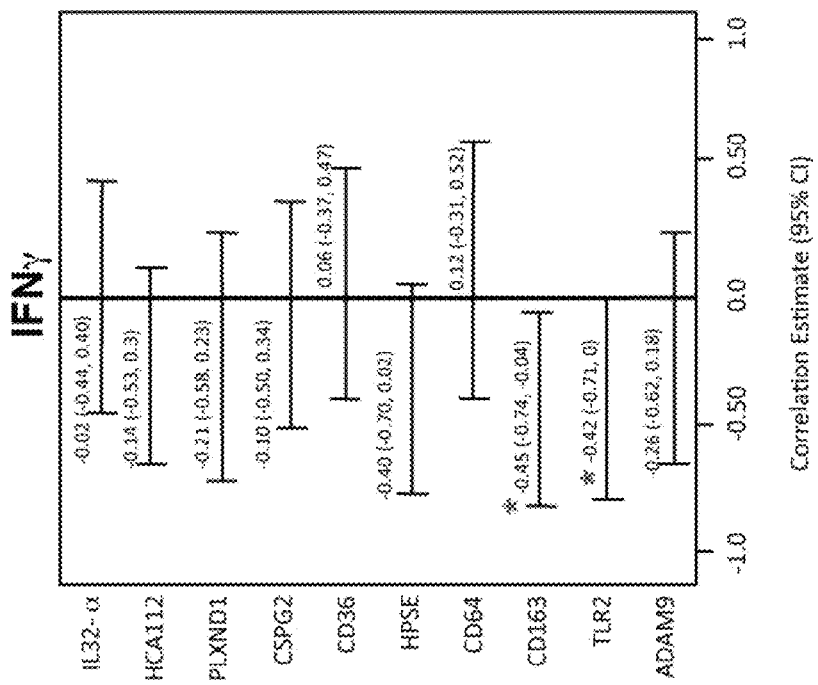
FIGS. 7A and 7B show the association of gene expression with serum cytokine concentration, interleukin 6 (IL-6) and interferon gamma (IFNγ). Spearman correlations with a Fisher's Z transformation are presented, with 95% confidence interval (CI).
Figure 7A:
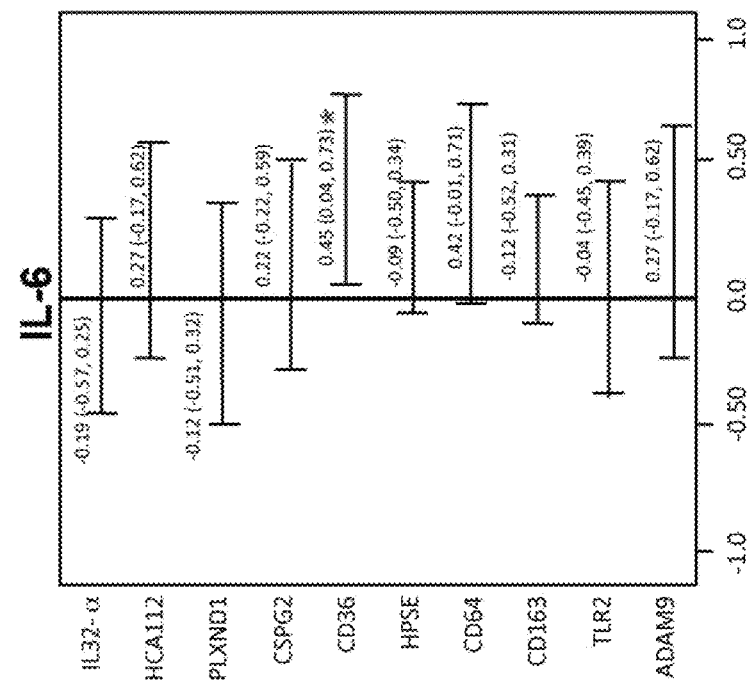

In addition, the association between transcript abundance, serum IL-6 (representing the acute-phase response), and IFNγ (representing bacterial clearance) cytokine concentrations was measured in cluster members who had serum available for testing. Serum collected at the same time of mRNA isolation was analyzed from Cluster 1 (n=6 of 10 total samples), Cluster 2 (n=9 of 37 samples), and Cluster 3 (n=7 of 10 samples). Gene expression of CD36, a co-receptor for the TLR2 heterodimer, was positively associated with serum IL-6 concentrations (r=0.45, p=0.03) (FIG. 7A). However, TLR2 and CD163 expression were negatively correlated with serum IFNγ concentrations (r=−0.42, p=0.047; r=−0.45, p=0.03) (FIG. 7B).

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following exemplary claims. Each publication and reference cited herein is incorporated herein by reference in its entirety.

REFERENCES

1. Patient registry: Annual Data Report. Cystic Fibrosis Foundation 2012; Bethesda, Md.
2. Davis P B, Drumm M, Konstan M W. Cystic fibrosis. Am J Respir Crit Care Med 1996; 154:1229-56.
3. Chmiel J F, Berger M, Konstan M W. The role of inflammation in the pathophysiology of CF lung disease. Clin Rev Allergy Immunol 2002; 23:5-27.
4. Sanders D B, Hoffman L R, Emerson J, et al. Return of FEV1 after pulmonary exacerbation in children with cystic fibrosis. Pediatr Pulmonol 2010; 45:127-34.
5. Sanders D B, Bittner R C, Rosenfeld M, Hoffman L R, Redding G J, Goss C H. Failure to recover to baseline pulmonary function after cystic fibrosis pulmonary exacerbation. Am J Respir Crit Care Med 2010; 182:627-32.
6. Waters V, Stanojevic S, Atenafu E G, et al. Effect of pulmonary exacerbations on long-term lung function decline in cystic fibrosis. Eur Respir J 2012; 40:61-6.
7. Sanders D B, Bittner R C, Rosenfeld M, Redding G J, Goss C H. Pulmonary exacerbations are associated with subsequent FEV1 decline in both adults and children with cystic fibrosis. Pediatr Pulmonol 2011; 46:393-400.
8. Shoki A H, Mayer-Hamblett N, Wilcox P G, Sin D D, Quon B S. Systematic review of blood biomarkers in cystic fibrosis pulmonary exacerbations. Chest 2013; 144: 1659-70.
9. Flume P A, Mogayzel P J, Jr., Robinson K A, et al. Cystic fibrosis pulmonary guidelines: treatment of pulmonary exacerbations. Am J Respir Crit Care Med 2009; 180: 802-8.
10. Saavedra M T, Hughes G J, Sanders L A, et al. Circulating RNA transcripts identify therapeutic response in cystic fibrosis lung disease. Am J Respir Crit Care Med 2008; 178:929-38.
11. Nick J A, Sanders L A, Ickes B, et al. Blood mRNA biomarkers for detection of treatment response in acute pulmonary exacerbations of cystic fibrosis. Thorax 2013; 68:929-37.
12. Foundation C F. Microbiology and infectious diseases in cystic fibrosis: V (Section 1). Bethesda, Md.; 1994.
13. Rosenfeld M, Emerson J, Williams-Warren J, et al. Defining a pulmonary exacerbation in cystic fibrosis. J Pediatr 2001; 139:359-65.
14. Singh D, Fox S M, Tal-Singer R, Bates S, Riley J H, Celli B. Altered gene expression in blood and sputum in COPD frequent exacerbators in the ECLIPSE cohort. PLoS One 2014; 9:e107381.
15. McGrath K W, Icitovic N, Boushey H A, et al. A large subgroup of mild-to-moderate asthma is persistently noneosinophilic. Am J Respir Crit Care Med 2012; 185: 612-9.
16. Carolan B J, Sutherland E R. Clinical phenotypes of chronic obstructive pulmonary disease and asthma: recent advances. J Allergy Clin Immunol 2013; 131:627-34; quiz 35.
17. Johnson C M, Tapping R I. Microbial products stimulate human Toll-like receptor 2 expression through histone modification surrounding a proximal NF-kappaB-binding site. J Biol Chem 2007; 282:31197-205.
18. Muller-Anstett M A, Muller P, Albrecht T, et al. Staphylococcal peptidoglycan co-localizes with Nod2 and TLR2 and activates innate immune response via both receptors in primary murine keratinocytes. PLoS One 2010; 5:e13153.
19. Fabriek B O, van Bruggen R, Deng D M, et al. The macrophage scavenger receptor CD163 functions as an innate immune sensor for bacteria. Blood 2009; 113:887-92.
20. Huang Z Y, Hunter S, Chien P, et al. Interaction of two phagocytic host defense systems: Fcgamma receptors and complement receptor 3. J Biol Chem 2011; 286:160-8.
21. Roychaudhuri R, Hergrueter A H, Polverino F, et al. ADAMS Is a Novel Product of Polymorphonuclear Neutrophils: Regulation of Expression and Contributions to Extracellular Matrix Protein Degradation during Acute Lung Injury J Immunol 2014; 193:2469-82.
22. Moser C, Kjaergaard S, Pressler T, Kharazmi A, Koch C, Hoiby N. The immune response to chronic *Pseudomonas aeruginosa* lung infection in cystic fibrosis patients is predominantly of the Th2 type. APMIS 2000; 108:329-35.
23. Brazova J, Sediva A, Pospisilova D, et al. Differential cytokine profile in children with cystic fibrosis. Clin Immunol 2005; 115:210-5.
24. Wojewodka G, De Sanctis J B, Bernier J, et al. Candidate markers associated with the probability of future pulmonary exacerbations in cystic fibrosis patients. PLoS One 2014; 9:e88567.
25. Liou T G, Adler F R, Keogh R H, et al. Sputum biomarkers and the prediction of clinical outcomes in patients with cystic fibrosis. PLoS One 2012; 7:e42748.
26. Downey D G, Martin S L, Dempster M, et al. The relationship of clinical and inflammatory markers to outcome in stable patients with cystic fibrosis. Pediatr Pulmonol 2007; 42:216-20.

27. Rosenthal M. Annual assessment spirometry, plethysmography, and gas transfer in cystic fibrosis: do they predict death or transplantation. Pediatr Pulmonol 2008; 43:945-52.
28. Kerem E, Reisman J, Corey M, Canny G J, Levison H. Prediction of mortality in patients with cystic fibrosis. N Engl J Med 1992; 326:1187-91.
29. Moffitt K L, Martin S L, Jones A M, et al. Inflammatory and immunological biomarkers are not related to survival in adults with Cystic Fibrosis. J Cyst Fibros 2014; 13:63-8.
30. George P M, Banya W, Pareek N, et al. Improved survival at low lung function in cystic fibrosis: cohort study from 1990 to 2007. BMJ 2011; 342:d1008.
31. Gray R D, Imrie M, Boyd A C, Porteous D, Innes J A, Greening A P. Sputum and serum calprotectin are useful biomarkers during CF exacerbation. J Cyst Fibros 2010; 9:193-8.
32. Sequeiros I M, Jarad N. Factors associated with a shorter time until the next pulmonary exacerbation in adult patients with cystic fibrosis. Chron Respir Dis 2012; 9:9-16.

What is claimed:

1. A method of determining pulmonary disease progression severity in a subject having cystic fibrosis and treating the subject, wherein the subject has experienced a pulmonary exacerbation, the method comprising
    a. obtaining a whole blood sample from the subject at the time of pulmonary exacerbation;
    b. detecting the mRNA expression level of each of the following genes: TLR2, ADAM9, PLXND1, CD163, CD36, CD64, CSPG2, IL32, HPSE, HCA112;
    c. determining the severity of the pulmonary disease progress in the subject by calculating a disease risk score of mild, moderate or severe pulmonary disease progression based on the subject's combined mRNA expression level of the genes from step (b) at the time of pulmonary exacerbation, wherein the subject's calculated disease risk score correlates to the risk score for mild, moderate or severe pulmonary disease progression at exacerbation; and
    d. treating the subject with treatments effective for treating mild, moderate or severe pulmonary disease progression.
2. The method of claim 1, wherein the mRNA expression level of the genes is detected by quantitative PCR or flow cytometery.
3. The method of claim 1, wherein a subject having severe pulmonary exacerbation disease progression will have an increased risk of morbidity.
4. The method of claim 1, wherein a subject having severe pulmonary exacerbation disease progression will have an increased risk of mortality.
5. The method of claim 1, wherein a subject having severe or moderate pulmonary exacerbation disease progression will have an increased risk for exacerbation recurrence.
6. The method of claim 1, wherein a subject having severe or moderate pulmonary exacerbation disease progression will have a shorter interval of exacerbation free time.
7. The method of claim 1, further comprising measuring the subject's forced expiratory volume ($FEV_1$) and/or C-reactive protein (CRP) levels.

* * * * *